(12) United States Patent
Bonutti et al.

(10) Patent No.: US 8,162,977 B2
(45) Date of Patent: Apr. 24, 2012

(54) METHOD FOR JOINING IMPLANTS

(75) Inventors: Peter M. Bonutti, Effingham, IL (US); Matthew J. Cremens, Effingham, IL (US)

(73) Assignee: P Tech, LLC., Effingham, IL (US)

( * ) Notice: Subject to any disclaimer, the term of this patent is extended or adjusted under 35 U.S.C. 154(b) by 854 days.

(21) Appl. No.: 11/932,602

(22) Filed: Oct. 31, 2007

(65) Prior Publication Data

US 2008/0108897 A1  May 8, 2008

Related U.S. Application Data

(63) Continuation of application No. 11/465,199, filed on Aug. 17, 2006, now Pat. No. 7,854,750, which is a continuation of application No. 10/228,855, filed on Aug. 27, 2002, now Pat. No. 7,094,251.

(51) Int. Cl.
*A61B 17/04* (2006.01)
(52) U.S. Cl. ...................................... 606/232
(58) Field of Classification Search .................. 606/113, 606/232, 300, 151
See application file for complete search history.

(56) References Cited

U.S. PATENT DOCUMENTS

| | | |
|---|---|---|
| 2,518,276 A | 8/1950 | Braward |
| 3,513,848 A | 5/1970 | Winston et al. |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,825,010 A | 7/1974 | McDonald |
| 3,875,652 A | 4/1975 | Arnold |
| 3,898,992 A | 8/1975 | Balamuth |
| 3,918,442 A | 11/1975 | Nikolaev et al. |
| 4,064,566 A | 12/1977 | Fletcher et al. |
| 4,089,071 A | 5/1978 | Kainberz et al. |
| 4,156,574 A | 5/1979 | Boben |
| 4,171,544 A | 10/1979 | Hench et al. |

(Continued)

FOREIGN PATENT DOCUMENTS

EP      1614525      1/2006

(Continued)

OTHER PUBLICATIONS

Copending U.S. Appl. No. 10/779,978, Response to Office Action Dec. 3, 2007.

(Continued)

*Primary Examiner* — Julian Woo
(74) *Attorney, Agent, or Firm* — Fleit Gibbons Gutman Bongini & Bianco, PL; Paul D. Bianco; Martin Fleit

(57) ABSTRACT

The present invention provides a method of securing a suture. The method includes providing a retainer having first and second sections. The first section has a central post, and the second section has a central bore dimensioned to receive the central post. The method also includes moving a suture through a passage in the first section, wrapping the suture around the central post, and moving the suture through a channel of the second section. The method further includes interconnecting the first and second sections with the central post positioned in the central bore and with the suture disposed between the first and second sections. Moreover, the method includes bonding the first and second sections together to secure the suture relative to the retainer.

20 Claims, 9 Drawing Sheets

U.S. PATENT DOCUMENTS

| | | |
|---|---|---|
| 4,199,864 A | 4/1980 | Ashman |
| 4,200,939 A | 5/1980 | Oser |
| 4,213,816 A | 7/1980 | Morris |
| 4,235,238 A | 11/1980 | Ogiu et al. |
| 4,281,649 A | 8/1981 | Derweduwen |
| 4,309,488 A | 1/1982 | Heide et al. |
| 4,351,069 A | 9/1982 | Ballintyn et al. |
| 4,365,356 A | 12/1982 | Broemer et al. |
| 4,409,974 A | 10/1983 | Freedland |
| 4,414,166 A | 11/1983 | Charlson et al. |
| 4,437,191 A | 3/1984 | Van der Zat et al. |
| 4,448,194 A | 5/1984 | DiGiovanni et al. |
| 4,456,005 A | 6/1984 | Lichty |
| 4,495,664 A | 1/1985 | Bianquaert |
| 4,501,031 A | 2/1985 | McDaniel et al. |
| 4,506,681 A | 3/1985 | Mundell |
| 4,514,125 A | 4/1985 | Stol |
| 4,526,173 A | 7/1985 | Sheehan |
| 4,535,772 A | 8/1985 | Sheehan |
| 4,547,327 A | 10/1985 | Bruins et al. |
| 4,556,350 A | 12/1985 | Bernhardt et al. |
| 4,599,085 A | 7/1986 | Riess et al. |
| 4,601,893 A | 7/1986 | Cardinal |
| 4,645,503 A | 2/1987 | Lin et al. |
| 4,657,460 A | 4/1987 | Bien |
| 4,659,268 A | 4/1987 | Del Mundo et al. |
| 4,662,068 A | 5/1987 | Polonsky |
| 4,662,887 A | 5/1987 | Turner et al. |
| 4,669,473 A | 6/1987 | Richards et al. |
| 4,705,040 A | 11/1987 | Mueller et al. |
| 4,718,909 A | 1/1988 | Brown |
| 4,722,948 A | 2/1988 | Sanderson |
| 4,741,330 A | 5/1988 | Hayhurst |
| 4,750,492 A | 6/1988 | Jacobs |
| 4,768,507 A | 9/1988 | Fischell et al. |
| 4,776,738 A | 10/1988 | Winston |
| 4,792,336 A | 12/1988 | Hiavacek et al. |
| 4,817,591 A | 4/1989 | Klause |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,841,960 A | 6/1989 | Garner |
| 4,843,112 A | 6/1989 | Gerhart |
| 4,901,721 A | 2/1990 | Hakki |
| 4,924,866 A | 5/1990 | Yoon |
| 4,932,960 A | 6/1990 | Green et al. |
| 4,935,026 A | 6/1990 | McFadden |
| 4,935,028 A | 6/1990 | Drews |
| 4,945,625 A | 8/1990 | Winston |
| 4,961,741 A | 10/1990 | Hayhurst |
| 4,963,151 A | 10/1990 | Ducheyne et al. |
| 4,990,161 A | 2/1991 | Kampner |
| 4,994,071 A | 2/1991 | MacGregor |
| 4,997,445 A | 3/1991 | Hodorek |
| 5,002,563 A | 3/1991 | Pyka et al. |
| 5,009,664 A | 4/1991 | Sievers |
| 5,019,090 A | 5/1991 | Pinchuk |
| 5,035,713 A | 7/1991 | Friis |
| 5,041,114 A | 8/1991 | Chapman et al. |
| 5,051,049 A | 9/1991 | Wills |
| 5,061,286 A | 10/1991 | Lyle |
| 5,078,731 A | 1/1992 | Hayhurst |
| 5,085,660 A | 2/1992 | Lin |
| 5,085,661 A | 2/1992 | Moss |
| 5,098,433 A | 3/1992 | Freedland |
| 5,098,436 A | 3/1992 | Ferrante et al. |
| 5,100,405 A | 3/1992 | McLaren |
| 5,102,417 A | 4/1992 | Palmaz |
| 5,108,399 A | 4/1992 | Eitenmuller et al. |
| 5,120,175 A | 6/1992 | Arbegast et al. |
| 5,133,732 A | 7/1992 | Wiktor |
| 5,156,613 A | 10/1992 | Sawyer |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,179,964 A | 1/1993 | Cook |
| 5,192,287 A | 3/1993 | Fournier et al. |
| 5,203,787 A | 4/1993 | Noblitt |
| 5,208,950 A | 5/1993 | Merritt |
| 5,209,776 A | 5/1993 | Bass et al. |
| 5,217,493 A | 6/1993 | Raad et al. |
| 5,234,006 A | 8/1993 | Eaton et al. |
| 5,236,438 A | 8/1993 | Wilk |
| 5,242,902 A | 9/1993 | Murphy et al. |
| 5,254,113 A | 10/1993 | Wilk |
| 5,258,015 A | 11/1993 | Li et al. |
| 5,258,016 A | 11/1993 | DiPoto et al. |
| 5,269,783 A | 12/1993 | Sander |
| 5,269,785 A | 12/1993 | Bonutti |
| 5,282,832 A | 2/1994 | Toso et al. |
| 5,290,281 A | 3/1994 | Tschakaloff |
| 5,306,280 A | 4/1994 | Bregen et al. |
| 5,324,308 A | 6/1994 | Pierce |
| 5,329,846 A | 7/1994 | Bonutti |
| 5,329,924 A | 7/1994 | Bonutti |
| 5,349,956 A | 9/1994 | Bonutti |
| 5,366,480 A | 11/1994 | Corriveaau et al. |
| 5,370,646 A | 12/1994 | Reese et al. |
| 5,372,146 A | 12/1994 | Branch |
| 5,376,126 A | 12/1994 | Lin |
| 5,383,883 A | 1/1995 | Wilk et al. |
| 5,383,905 A | 1/1995 | Golds et al. |
| 5,391,173 A | 2/1995 | Wilk |
| 5,403,312 A | 4/1995 | Yates et al. |
| 5,403,348 A | 4/1995 | Bonutti |
| 5,413,585 A | 5/1995 | Pagedas |
| 5,417,712 A | 5/1995 | Whittaker et al. |
| 5,423,796 A | 6/1995 | Shikhman et al. |
| 5,439,470 A | 8/1995 | Li |
| 5,441,538 A | 8/1995 | Bonutti |
| 5,443,512 A | 8/1995 | Parr et al. |
| 5,449,372 A | 9/1995 | Schmaltz et al. |
| 5,449,382 A | 9/1995 | Dayton |
| 5,458,653 A | 10/1995 | Davison |
| 5,464,426 A | 11/1995 | Bonutti |
| 5,464,427 A | 11/1995 | Curtis et al. |
| 5,472,444 A | 12/1995 | Huebner et al. |
| 5,474,554 A | 12/1995 | Ku |
| 5,478,351 A | 12/1995 | Meade et al. |
| 5,487,844 A | 1/1996 | Fujita |
| 5,504,977 A | 4/1996 | Weppner et al. |
| 5,505,735 A | 4/1996 | Li |
| 5,527,341 A | 6/1996 | Gogolewski et al. |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,540,718 A | 7/1996 | Bartlett |
| 5,542,423 A | 8/1996 | Bonutti |
| 5,545,180 A | 8/1996 | Le et al. |
| 5,549,630 A | 8/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,601,557 A * | 2/1997 | Hayhurst ..................... 606/232 |
| 5,620,461 A | 4/1997 | Muijs Van De Moer et al. |
| 5,626,612 A | 5/1997 | Bartlett |
| 5,628,751 A | 5/1997 | Sander et al. |
| 5,630,824 A | 5/1997 | Hart |
| 5,643,274 A | 7/1997 | Sander et al. |
| 5,643,295 A | 7/1997 | Yoon |
| 5,645,553 A | 7/1997 | Kolesa et al. |
| 5,651,377 A | 7/1997 | O'Donnell, Jr. |
| 5,660,225 A | 8/1997 | Saffran |
| 5,665,109 A | 9/1997 | Yoon |
| 5,667,513 A | 9/1997 | Torrie et al. |
| 5,669,917 A | 9/1997 | Sauer et al. |
| 5,681,351 A | 10/1997 | Jamiolkowski et al. |
| 5,690,654 A | 11/1997 | Ovil |
| 5,690,655 A | 11/1997 | Hart et al. |
| 5,697,950 A | 12/1997 | Fucci et al. |
| 5,702,397 A | 12/1997 | Gonle et al. |
| 5,713,903 A | 2/1998 | Sander et al. |
| 5,713,921 A | 2/1998 | Bonutti |
| 5,718,717 A | 2/1998 | Bonutti |

| Patent Number | Date | Inventor |
|---|---|---|
| 5,720,747 A | 2/1998 | Burke |
| 5,720,753 A | 2/1998 | Sander et al. |
| 5,725,556 A | 3/1998 | Moser et al. |
| 5,725,582 A | 3/1998 | Bevan |
| 5,735,875 A | 4/1998 | Bonutti et al. |
| 5,735,877 A | 4/1998 | Pagedas |
| 5,752,974 A | 5/1998 | Rhee et al. |
| 5,769,894 A | 6/1998 | Ferragamo |
| 5,779,706 A | 7/1998 | Tschakaloff |
| 5,782,862 A | 7/1998 | Bonutti |
| 5,785,713 A | 7/1998 | Jobe |
| 5,797,931 A * | 8/1998 | Bito et al. ............ 606/151 |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,823,994 A | 10/1998 | Sharkey et al. |
| 5,836,897 A | 11/1998 | Sakural et al. |
| 5,843,178 A | 12/1998 | Vanney et al. |
| 5,845,645 A | 12/1998 | Bonutti |
| 5,866,634 A | 2/1999 | Tokushige |
| 5,874,235 A | 2/1999 | Chan et al. |
| 5,879,372 A | 3/1999 | Bartlett |
| 5,891,166 A | 4/1999 | Schervinsky |
| 5,893,880 A | 4/1999 | Egan et al. |
| 5,899,921 A | 5/1999 | Caspari et al. |
| 5,906,625 A | 5/1999 | Bito et al. |
| 5,908,429 A | 6/1999 | Yoon |
| 5,919,215 A | 7/1999 | Wiklund et al. |
| 5,921,986 A | 7/1999 | Bonutti |
| 5,928,244 A | 7/1999 | Tovey et al. |
| 5,928,267 A | 7/1999 | Bonutti et al. |
| 5,941,901 A | 8/1999 | Egan |
| 5,948,001 A | 9/1999 | Larsen |
| 5,948,002 A | 9/1999 | Bonutti |
| 5,951,590 A | 9/1999 | Goldfarb |
| 5,964,765 A | 10/1999 | Fenton et al. |
| 5,968,047 A | 10/1999 | Reed |
| 5,980,520 A | 11/1999 | Vancaillie |
| 5,984,929 A | 11/1999 | Bashiri et al. |
| 5,989,282 A | 11/1999 | Bonutti |
| 5,993,477 A | 11/1999 | Vaitekunas et al. |
| 6,010,525 A | 1/2000 | Bonutti et al. |
| 6,045,551 A | 4/2000 | Bonutti |
| 6,056,751 A * | 5/2000 | Fenton, Jr. ............ 606/232 |
| 6,056,772 A | 5/2000 | Bonutti |
| 6,059,817 A | 5/2000 | Bonutti et al. |
| 6,059,827 A | 5/2000 | Fenton |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,077,277 A | 6/2000 | Mollenauer et al. |
| 6,077,292 A | 6/2000 | Bonutti |
| 6,080,161 A | 6/2000 | Eaves, III et al. |
| 6,086,608 A | 7/2000 | Ek et al. |
| 6,099,531 A | 8/2000 | Bonutti |
| 6,099,537 A | 8/2000 | Sugai et al. |
| 6,099,552 A | 8/2000 | Adams |
| 6,102,850 A | 8/2000 | Wang et al. |
| 6,106,545 A | 8/2000 | Egan |
| 6,120,536 A | 9/2000 | Ding et al. |
| 6,139,320 A | 10/2000 | Hahn |
| 6,149,669 A | 11/2000 | Li |
| 6,159,234 A | 12/2000 | Bonutti et al. |
| 6,171,307 B1 | 1/2001 | Orlich |
| 6,174,324 B1 | 1/2001 | Egan et al. |
| 6,179,840 B1 | 1/2001 | Bowman |
| 6,190,401 B1 | 2/2001 | Green |
| 6,217,591 B1 | 4/2001 | Egan et al. |
| 6,224,593 B1 | 5/2001 | Ryan |
| 6,228,086 B1 | 5/2001 | Wahl et al. |
| 6,231,592 B1 | 5/2001 | Bonutti et al. |
| 6,264,675 B1 | 7/2001 | Brotz |
| 6,267,761 B1 | 7/2001 | Ryan |
| 6,273,717 B1 | 8/2001 | Hahn et al. |
| 6,286,746 B1 | 9/2001 | Egan et al. |
| 6,293,961 B2 | 9/2001 | Schwartz et al. |
| 6,306,159 B1 | 10/2001 | Schwartz et al. |
| 6,348,056 B1 | 2/2002 | Bates et al. |
| 6,358,271 B1 | 3/2002 | Egan et al. |
| 6,368,343 B1 | 4/2002 | Bonutti et al. |
| 6,371,957 B1 | 4/2002 | Amrein et al. |
| 6,409,742 B1 | 6/2002 | Fulton, III |
| 6,409,743 B1 | 6/2002 | Fenton |
| 6,423,088 B1 | 7/2002 | Fenton |
| 6,432,115 B1 | 8/2002 | Mollenauer et al. |
| 6,447,516 B1 | 9/2002 | Bonutti |
| 6,461,360 B1 | 10/2002 | Adams |
| 6,468,293 B2 | 10/2002 | Bonutti et al. |
| 6,475,230 B1 | 11/2002 | Bonutti |
| 6,488,196 B1 | 12/2002 | Fenton |
| 6,503,259 B2 | 1/2003 | Huxel et al. |
| 6,527,774 B2 | 3/2003 | Lieberman |
| 6,545,390 B1 | 4/2003 | Hahn et al. |
| 6,554,852 B1 | 4/2003 | Oberlander |
| 6,557,426 B2 | 5/2003 | Reinemann et al. |
| 6,569,187 B1 | 5/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,592,609 B1 | 7/2003 | Bonutti |
| 6,605,090 B1 | 8/2003 | Trieu et al. |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,632,245 B2 | 10/2003 | Kim |
| 6,635,073 B2 | 10/2003 | Bonutti |
| 6,666,877 B2 | 12/2003 | Morgan et al. |
| 6,669,705 B2 | 12/2003 | Westhaver et al. |
| 6,702,821 B2 | 3/2004 | Bonutti |
| 6,709,457 B1 | 3/2004 | Otte |
| 6,719,765 B2 | 4/2004 | Bonutti |
| 6,722,552 B2 | 4/2004 | Fenton |
| 6,770,078 B2 | 8/2004 | Bonutti |
| 6,786,989 B2 | 9/2004 | Torriani et al. |
| 6,818,010 B2 | 11/2004 | Eichhorn et al. |
| 6,890,334 B2 | 5/2005 | Brace et al. |
| 6,893,434 B2 | 5/2005 | Fenton et al. |
| 6,913,666 B1 | 7/2005 | Aeschlimann et al. |
| 6,921,264 B2 | 7/2005 | Mayer et al. |
| 6,923,824 B2 | 8/2005 | Morgan et al. |
| 6,932,835 B2 | 8/2005 | Bonutti |
| 6,944,111 B2 | 9/2005 | Nakamura et al. |
| 6,955,540 B2 | 10/2005 | Mayer et al. |
| 6,981,983 B1 | 1/2006 | Rosenblatt et al. |
| 7,001,411 B1 | 2/2006 | Dean |
| 7,008,226 B2 | 3/2006 | Mayer et al. |
| 7,018,380 B2 | 3/2006 | Cole |
| 7,048,755 B2 | 5/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,329,263 B2 | 2/2008 | Bonutti |
| 7,335,205 B2 | 2/2008 | Aeshcliamann |
| 7,429,266 B2 | 9/2008 | Bonutti |
| 7,510,895 B2 | 3/2009 | Raterman |
| 2002/0183762 A1 | 12/2002 | Anderson et al. |
| 2003/0118518 A1 | 6/2003 | Hahn et al. |
| 2003/0167072 A1 | 9/2003 | Oberlander |
| 2003/0181800 A1 | 9/2003 | Bonutti |
| 2004/0030341 A1 | 2/2004 | Aeschlimann et al. |
| 2004/0098050 A1 | 5/2004 | Foerster et al. |
| 2004/0220616 A1 | 11/2004 | Bonutti |
| 2004/0230223 A1 | 11/2004 | Bonutti |
| 2005/0033366 A1 | 2/2005 | Cole |
| 2005/0126680 A1 | 6/2005 | Aeschlimann et al. |
| 2005/0216059 A1 | 9/2005 | Bonutti |
| 2005/0240190 A1 | 10/2005 | Gall et al. |
| 2005/0246021 A1 | 11/2005 | Ringeisen et al. |
| 2005/0267534 A1 | 12/2005 | Bonutti |
| 2006/0009855 A1 | 1/2006 | Goble et al. |
| 2006/0015101 A1 | 1/2006 | Warburton et al. |

| | | | |
|---|---|---|---|
| 2006/0024357 | A1 | 2/2006 | Carpenter et al. |
| 2006/0122600 | A1 | 6/2006 | Cole |
| 2006/0167495 | A1 | 7/2006 | Bonutti |
| 2006/0212073 | A1 | 9/2006 | Bonutti |
| 2006/0217765 | A1 | 9/2006 | Bonutti |
| 2006/0235470 | A1 | 10/2006 | Bonutti |
| 2006/0241695 | A1 | 10/2006 | Bonutti |
| 2007/0118129 | A1 | 5/2007 | Fraser et al. |
| 2007/0270833 | A1 | 11/2007 | Bonutti |
| 2008/0039845 | A1 | 2/2008 | Bonutti |
| 2008/0108916 | A1 | 5/2008 | Bonutti |
| 2008/0132950 | A1 | 6/2008 | Lange |
| 2008/0140117 | A1 | 6/2008 | Bonutti |
| 2008/0269753 | A1 | 10/2008 | Cannestra |
| 2008/0269808 | A1 | 10/2008 | Gall et al. |
| 2009/0024161 | A1 | 1/2009 | Bonutti |

FOREIGN PATENT DOCUMENTS

| | | |
|---|---|---|
| EP | 1988837 | 8/2007 |
| EP | 2134294 | 12/2009 |
| JP | 8140982 | 6/1996 |
| WO | 91/12779 | 9/1991 |
| WO | WO 95/31941 | 11/1995 |
| WO | 2007/092869 A2 | 8/2007 |
| WO | 2008/116203 | 9/2008 |
| WO | 2009/029908 | 3/2009 |

OTHER PUBLICATIONS

Copending U.S. Appl. No. 10/779,978, Response to Office Action Mar. 25, 2008.
Copending U.S. Appl. No. 10/779,978, Non-Final Rejection mailed Jun. 18, 2008.
Copending U.S. Appl. No. 10/779,978, Response to Office Action Oct. 20, 2008.
Copending U.S. Appl. No. 10/779,978, Final Rejection mailed Feb. 3, 2009.
Copending U.S. Appl. No. 10/779,978, Request for Continued Examination Jul. 6, 2009.
Copending U.S. Appl. No. 10/779,978, Response to Office Action Jul. 6, 2009.
Copending U.S. Appl. No. 10/779,978, Non-Final Rejection mailed Oct. 1, 2009.
Copending U.S. Appl. No. 10/779,978, Response to Office Action Feb. 1, 2010.
Copending U.S. Appl. No. 10/779,978, Final Rejection mailed May 14, 2010.
Copending U.S. Appl. No. 10/797,685, filed Mar. 9, 2004.
Copending U.S. Appl. No. 10/797,685, Non-Final Rejection mailed Nov. 17, 2006.
Copending U.S. Appl. No. 10/797,685, Response to Office Action Feb. 20, 2007.
Copending U.S. Appl. No. 10/797,685, Final Rejection mailed Apr. 25, 2007.
Copending U.S. Appl. No. 10/797,685, Response to Office Action Aug. 27, 2007.
Copending U.S. Appl. No. 10/797,685, Examiner Interview Summary mailed Sep. 11, 2007.
Copending U.S. Appl. No. 11/874,323, filed Oct. 18, 2007.
Copending U.S. Appl. No. 11/671,556, filed Feb. 6, 2007.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/671,556, Non-Final Rejection mailed Feb. 22, 2010.
Copending U.S. Appl. No. 11/416,618, filed May 3, 2006.
Copending U.S. Appl. No. 11/416,618, Non-Final Rejection mailed Nov. 26, 2008.
Copending U.S. Appl. No. 11/416,618, Response to Office Action Mar. 26, 2009.
Copending U.S. Appl. No. 11/416,618, Final Rejection mailed Jun. 24, 2009.
Copending U.S. Appl. No. 11/416,618, Response to Office Action Sep. 24, 2009.
Copending U.S. Appl. No. 11/416,618, Non-Final Rejection mailed Oct. 13, 2009.
Copending U.S. Appl. No. 11/416,618, Response to Office Action Mar. 15, 2010.
Copending U.S. Appl. No. 11/416,618, Examiner Interview Summary mailed Apr. 15, 2010.
Copending U.S. Appl. No. 11/416,618, Response to Office Action Apr. 16, 2010.
Copending U.S. Appl. No. 11/689,670, filed Mar. 22, 2007.
Copending U.S. Appl. No. 11/689,670, Requirement for Restriction Mar. 15, 2010.
Copending U.S. Appl. No. 11/689,670, Response to Office Action Apr. 15, 2010.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arcioscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford projection, compact oxford english dicitionary: projection, Mar. 30, 2003
Ask Oxford projection, compact oxford english dicitionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
IPER—Internation Preliminary Report on Patentability, WO/2007/092869, published Aug. 12, 2008 for PCT/US2007/061730.
Written Opinion WO/2007/092869 dated Aug. 7, 2008 for PCT/US2007/061730.
Copending U.S. Appl. No. 09/556,458, filed May 3, 2000.
Copending U.S. Appl. No. 09/556,458, Non-Final Rejection mailed Sep. 25, 2002.
Copending U.S. Appl. No. 09/556,458, Response to Office Action Dec. 26, 2002.
Copending U.S. Appl. No. 10/614,352, filed Jul. 7, 2003.
Copending U.S. Appl. No. 10/614,352, Non-Final Rejection mailed Dec. 1, 2005.
Copending U.S. Appl. No. 10/614,352, Response to Office Action Mar. 1, 2006.
Copending U.S. Appl. No. 10/614,352, Non-Final Rejection mailed Aug. 1, 2006.
Copending U.S. Appl. No. 10/614,352, Response to Office Action Nov. 1, 2006.
Copending U.S. Appl. No. 10/614,352, Final Rejection mailed Jan. 25, 2007.
Copending U.S. Appl. No. 10/614,352, Response to Office Action Mar. 26, 2007.
Copending U.S. Appl. No. 10/614,352, Non-Final Rejection mailed Apr. 17, 2007.
Copending U.S. Appl. No. 10/614,352, Response to Office Action Jul. 17, 2007.
Copending U.S. Appl. No. 10/614,352, Examiner Interview Summary Jul. 31, 2007.
Copending U.S. Appl. No. 10/614,352, Final Rejection mailed Oct. 2, 2007.

Copending U.S. Appl. No. 10/614,352, Request for Continued Examination Oct. 30, 2007.
Copending U.S. Appl. No. 10/614,352, Response to Office Action Oct. 30, 2007.
Copending U.S. Appl. No. 10/614,352, Non-Final Rejection mailed Jan. 15, 2008.
Copending U.S. Appl. No. 10/614,352, Response to Office Action May 15, 2008.
Copending U.S. Appl. No. 10/614,352, Non-Final Rejection mailed Aug. 21, 2008.
Copending U.S. Appl. No. 10/614,352, Response to Office Action Dec. 22, 2008.
Copending U.S. Appl. No. 10/614,352, Final Rejection mailed Apr. 14, 2009.
Copending U.S. Appl. No. 10/614,352, Request for Continued Examination Sep. 14, 2009.
Copending U.S. Appl. No. 10/614,352, Response to Office Action Sep. 14, 2009.
Copending U.S. Appl. No. 10/614,352, Non-Final Rejection mailed Nov. 24, 2009.
Copending U.S. Appl. No. 10/614,352, Response to Office Action Apr. 26, 2010.
Copending U.S. Appl. No. 11/931,823, filed Oct. 31, 2007.
Copending U.S. Appl. No. 09/789,621, filed Feb. 21, 2001.
Copending U.S. Appl. No. 10/413,696, filed Apr. 14, 2003.
Copending U.S. Appl. No. 10/413,696, Requirement for Restriction Jun. 8, 2005.
Copending U.S. Appl. No. 10/413,696, Response to Office Action Jul. 5, 2005.
Copending U.S. Appl. No. 10/413,696, Non-Final Rejection mailed Sep. 23, 2005.
Copending U.S. Appl. No. 10/413,696, Response to Office Action Dec. 20, 2005.
Copending U.S. Appl. No. 11/460,650, filed Jul. 28, 2006.
Copending U.S. Appl. No. 11/460,650, Non-Final Rejection mailed May 30, 2007.
Copending U.S. Appl. No. 11/460,650, Response to Office Action Oct. 1, 2007.
Copending U.S. Appl. No. 11/460,650, Non-Final Rejection mailed Dec. 28, 2007.
Copending U.S. Appl. No. 11/460,650, Response to Office Action Mar. 28, 2008.
Copending U.S. Appl. No. 11/460,650, Final Rejection mailed Aug. 29, 2008.
Copending U.S. Appl. No. 11/460,650, Request for Continued Examination Jan. 29, 2009.
Copending U.S. Appl. No. 11/460,650, Response to Office Action Jan. 29, 2009.
Copending U.S. Appl. No. 11/460,650, Non-Final Rejection mailed Mar. 10, 2009.
Copending U.S. Appl. No. 11/460,650, Response to Office Action Jun. 10, 2009.
Copending U.S. Appl. No. 11/460,650, Non-Final Rejection mailed Sep. 16, 2009.
Copending U.S. Appl. No. 11/460,650, Examiner Interview Summary mailed Dec. 23, 2009.
Copending U.S. Appl. No. 11/460,650, Response to Office Action Jan. 12, 2010.
Copending U.S. Appl. No. 11/460,650, Final Rejection mailed Apr. 20, 2010.
Copending U.S. Appl. No. 11/461,110, filed Jul. 31, 2006.
Copending U.S. Appl. No. 11/461,110, Non-Final Rejection mailed May 14, 2007.
Copending U.S. Appl. No. 11/461,110, Response to Office Action Oct. 15, 2007.
Copending U.S. Appl. No. 11/461,110, Final Rejection mailed Dec. 12, 2007.
Copending U.S. Appl. No. 11/456,132, filed Jul. 7, 2006.
Copending U.S. Appl. No. 11/456,132, Non-Final Rejection mailed Jun. 18, 2007.
Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Request for Continued Examination Jun. 11, 2008.
Copending U.S. Appl. No. 11/456,132, Response to Office Action Jun. 11, 2008.
Copending U.S. Appl. No. 11/456,132, Non-Final Rejection mailed Oct. 7, 2008.
Copending U.S. Appl. No. 11/456,132, Response to Office Action Jan. 7, 2009.
Copending U.S. Appl. No. 11/456,132, Non-Final Rejection mailed Mar. 13, 2009.
Copending U.S. Appl. No. 11/456,132, Response to Office Action Aug. 13, 2009.
Copending U.S. Appl. No. 11/456,132, Examiner Interview Summary mailed Aug. 28, 2009.
Copending U.S. Appl. No. 11/456,132, Final Rejection mailed Dec. 18, 2009.
Copending U.S. Appl. No. 11/456,132, Response to Office Action Apr. 19, 2010.
Copending U.S. Appl. No. 11/456,221, filed Jul. 10, 2006.
Copending U.S. Appl. No. 11/456,221, Non-Final Rejection mailed Jul. 9, 2007.
Copending U.S. Appl. No. 11/456,221, Response to Office Action Nov. 9, 2007.
Copending U.S. Appl. No. 11/456,221, Final Rejection mailed Feb. 22, 2008.
Copending U.S. Appl. No. 11/456,221, Response to Office Action May 22, 2008.
Copending U.S. Appl. No. 11/456,221, Request for Continued Examintation Jun. 19, 2008.
Copending U.S. Appl. No. 11/456,221, Non-Final Rejection mailed Oct. 29, 2008.
Copending U.S. Appl. No. 11/456,221, Response to Office Action Mar. 30, 2009.
Copending U.S. Appl. No. 11/456,221, Non-Final Rejection mailed Jul. 6, 2009.
Copending U.S. Appl. No. 11/456,221, Response to Office Action Jan. 6, 2010.
Copending U.S. Appl. No. 11/456,221, Final Rejection mailed Mar. 24, 2010.
Copending U.S. Appl. No. 11/932,051, filed Oct. 31, 2007.
Copending U.S. Appl. No. 11/932,051, Requirement for Restriction Jan. 22, 2010.
Copending U.S. Appl. No. 10/228,855, filed Aug. 27, 2002.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, filed Aug. 19, 2006.
Copending U.S. Appl. No. 11/465,199, Non-Final Rejecrion mailed Dec. 28, 2009.
Copending U.S. Appl. No. 10/779,978, Non-Final Rejection mailed Aug. 3, 2007.
Copending U.S. Appl. No. 10/780,444, filed Feb. 17, 2004.
Copending U.S. Appl. No. 10/780,444, Requirement for Restriction Apr. 10, 2007.
Copending U.S. Appl. No. 10/780,444, Response to Office Action May 10, 2007.
Copending U.S. Appl. No. 10/780,444, Requirement for Restriction Sep. 12, 2007.
Copending U.S. Appl. No. 10/780,444, Response to Office Action Oct. 12, 2007.
Copending U.S. Appl. No. 10/780,444, Non-Final Rejection mailed Mar. 11, 2008.
Copending U.S. Appl. No. 10/780,444, Response to Office Action Jul. 9, 2008.
Copending U.S. Appl. No. 10/780,444, Final Rejection mailed Dec. 23, 2008.
Copending U.S. Appl. No. 10/780,444, Response to Office Action Apr. 23, 2009.
Copending U.S. Appl. No. 10/780,444, Request for Continued Examination Apr. 23, 2009.

Copending U.S. Appl. No. 10/780,444, Non-Final Rejection mailed Jul. 7, 2009.
Copending U.S. Appl. No. 10/780,444, Examiner Interview Summary mailed Nov. 20, 2009.
Copending U.S. Appl. No. 10/780,444, Response to Office Action Dec. 4, 2009.
Copending U.S. Appl. No. 10/780,444, Final Rejection mailed Mar. 30, 2010.
Copending U.S. Appl. No. 10/779,978 , filed Feb. 17, 2004.
Copending U.S. Appl. No. 10/779,978, Requirement for Restriction Apr. 20, 2007.
Copending U.S. Appl. No. 10/779,978, Response to Office Action May 21, 2007.
Copending U.S. Appl. No. 11/461,110, Request for Continued Examination Mar. 12, 2008.
Copending U.S. Appl. No. 11/461,110, Response to Office Action Mar. 12, 2008.
Copending U.S. Appl. No. 11/461,110, Non-Final Rejection mailed Jun. 6, 2008.
Copending U.S. Appl. No. 11/461,110, Response to Office Action Oct. 6, 2008.
Copending U.S. Appl. No. 11/461,110, Non-Final Rejection mailed Apr. 22, 2009.
Copending U.S. Appl. No. 11/461,110, Response to Office Action Sep. 22, 2009.
Copending U.S. Appl. No. 11/461,110, Final Rejection mailed Dec. 8, 2009.
Copending U.S. Appl. No. 11/930,621 , filed Oct. 31, 2007.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397, filed Mar. 13, 2000.
Copending U.S. Appl. No. 09/524,397, Non-Final Rejection mailed Dec. 18, 2000.
Copending U.S. Appl. No. 09/524,397, Response to Office Action Mar. 19, 2001.
Copending U.S. Appl. No. 09/524,397, Final Rejection mailed Jun. 13, 2001.
Copending U.S. Appl. No. 09/524,397, Response to Office Action Oct. 15, 2001.
Copending U.S. Appl. No. 10/076,919, filed Feb. 14, 2002.
Copending U.S. Appl. No. 10/458,117, filed Jun. 10, 2003.
Copending U.S. Appl. No. 10/458,117, Non-Final Rejection mailed Mar. 22, 2005.
Copending U.S. Appl. No. 10/458,117, Response to Office Action Jun. 22, 2005.
Copending U.S. Appl. No. 10/458,117, Final Rejection mailed Sep. 6, 2005.
Copending U.S. Appl. No. 10/458,117, Response to Office Action Nov. 8, 2005.
Copending U.S. Appl. No. 10/458,117, Advisory Actiom Jan. 20, 2006.
Copending U.S. Appl. No. 10/458,117, Request for Continued Examination Feb. 21, 2006.
Copending U.S. Appl. No. 10/458,117, Non-Final Rejection mailed Nov. 15, 2006.
Copending U.S. Appl. No. 10/458,117, Response to Office Action Feb. 13, 2007.
Copending U.S. Appl. No. 10/458,117, Final Rejection mailed May 3, 2007.
Copending U.S. Appl. No. 10/458,117, Request for Continued Examination Aug. 3, 2007.
Copending U.S. Appl. No. 10/458,117, Response to Office Action Aug. 3, 2007.
Copending U.S. Appl. No. 10/458,117, Request for Conitinued Examination Feb. 26, 2008.
Copending U.S. Appl. No. 10/458,117, Examiner Interview Summary mailed May 16, 2008.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO/2009/029908, published May 3, 2009 for PCT/US08/029908.
ISR—International Search Report, WO /2009/029908, published May 3, 2009 for PCT/US08/029908.
IPER—Internation Preliminary Report on Patentability, WO/2009/029908, published Mar. 2, 2010 for PCT/US08/029908.
Written Opinion WO/2009/029908 dated Feb. 28, 2010 for PCT/US08/029908.
Canadian Patent Application #2641580 equivalent to U.S. Appl. No. 11/671,556, P. Bonutti, Aug. 6, 2008.
Canadian Patent Application #2680827 equivalent to U.S. Appl. No. 11/689,670, P. Bonutti, Sep. 22, 2009.
Canadian Patent Application #2698057 equivalent to U.S. Appl. No. 12/202,210, P. Bonutti, Aug. 26, 2010.
European Patent Application #08828652 equivalent to U.S. Appl. No. 12/202,210, P. Bonutti, Aug. 29, 2008.
ISR—International Search Report PCT/US2010/025263 completed Apr. 13, 2010.
Written Opinion for PCT/US2010/025263 completed Apr. 13, 2010.
Copending U.S. Appl. No. 11/461,110, Request for Continued Examination Jun. 8, 2010.
Copending U.S. Appl. No. 11/461,110, Response to Office Action Jun. 8, 2010.
Copending U.S. Appl. No. 11/930,621, Final Rejection Jun. 22, 2010.
Copending U.S. Appl. No. 11/465,199, Response to Office Action Jun. 28, 2010.
Copending U.S. Appl. No. 12/711,540, filed Feb. 24, 2010.
Copending U.S. Appl. No. 11/931,823 RestrictionElect dated Jun. 8, 2010.
Copending U.S. Appl. No. 11/931,823 Response to Office Action Aug. 9, 2010.
Copending U.S. Appl. No. 11/931,823 Office Action mailed Nov. 24, 2010.
Copending U.S. Appl. No. 11/416,618, Request for Continued Examination Dec. 8, 2011.
Copending U.S. Appl. No. 11/689,670, Response to Office Action Jan. 3, 2011.
Copending U.S. Appl. No. 11/370,775, Request for Continued Examination Jan. 10, 2011.
Copending U.S. Appl. No. 10/779,978 Non-Final Office Action mailed Jan. 13, 2011.
Copending U.S. Appl. No. 11/671,556 Final Office Action mailed Nov. 12, 2010.
Copending U.S. Appl. No. 11/689,670, Final Office Action mailed Mar. 17, 2011.
Copending U.S. Appl. No. 11/456,132, Response to Office Action Apr. 14, 2011.
Copending U.S. Appl. No. 11/932,907, non-final Office Action Nov. 17, 2010.
Copending U.S. Appl. No. 11/932,907, Response to Office Action Apr. 18, 2011.

* cited by examiner

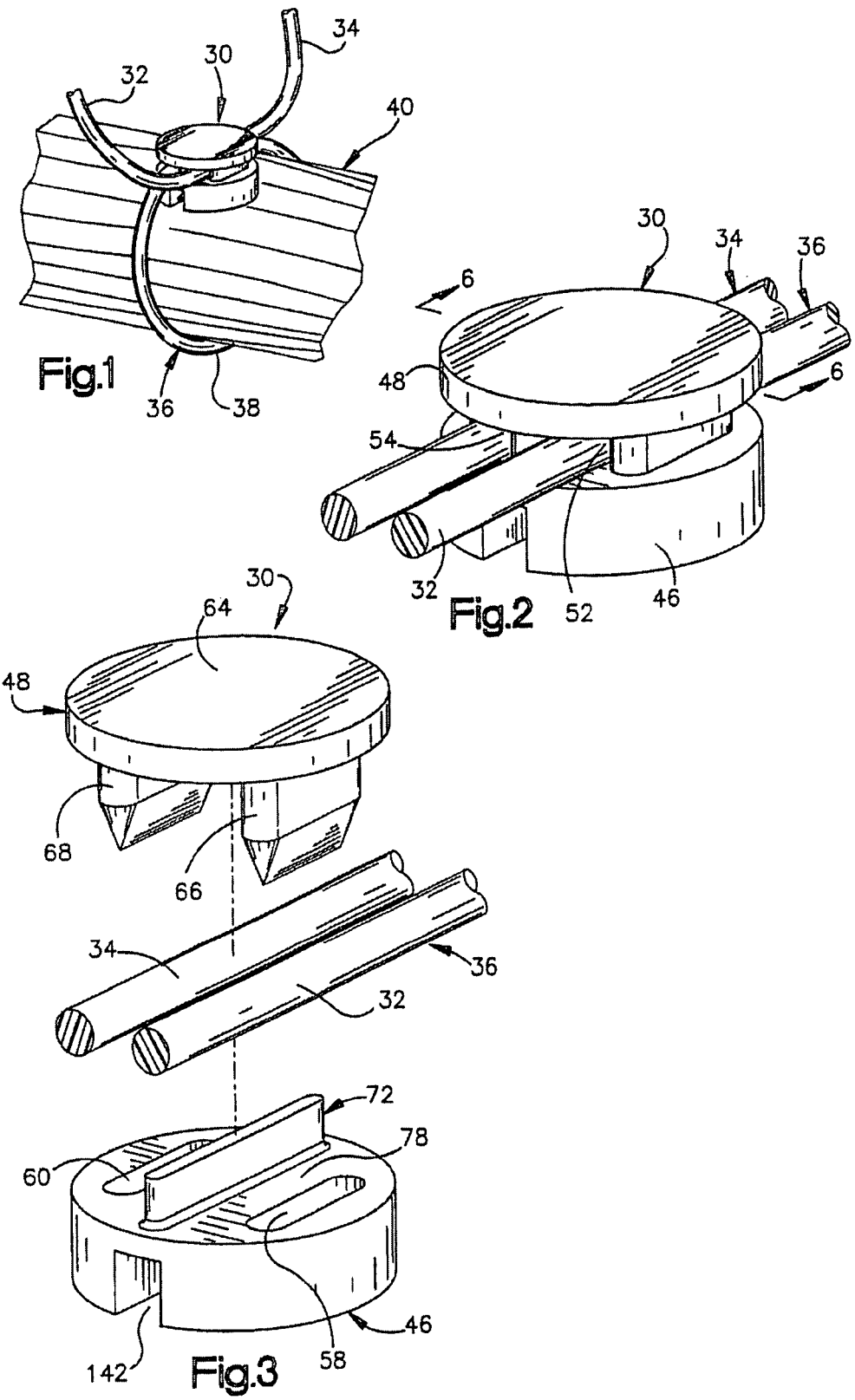

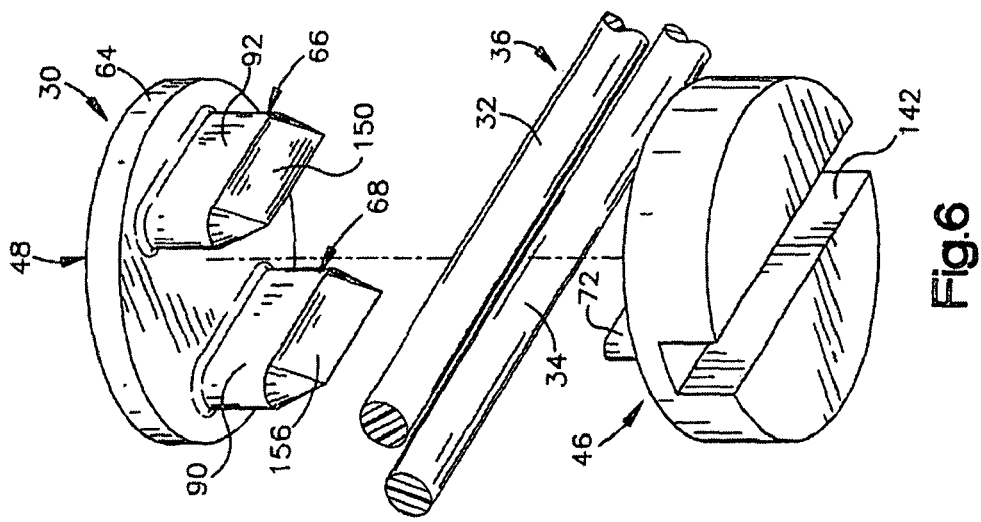
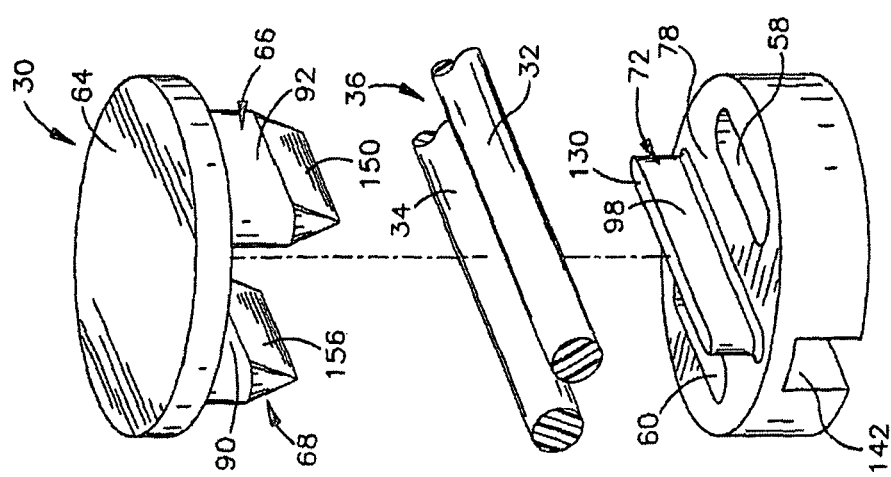
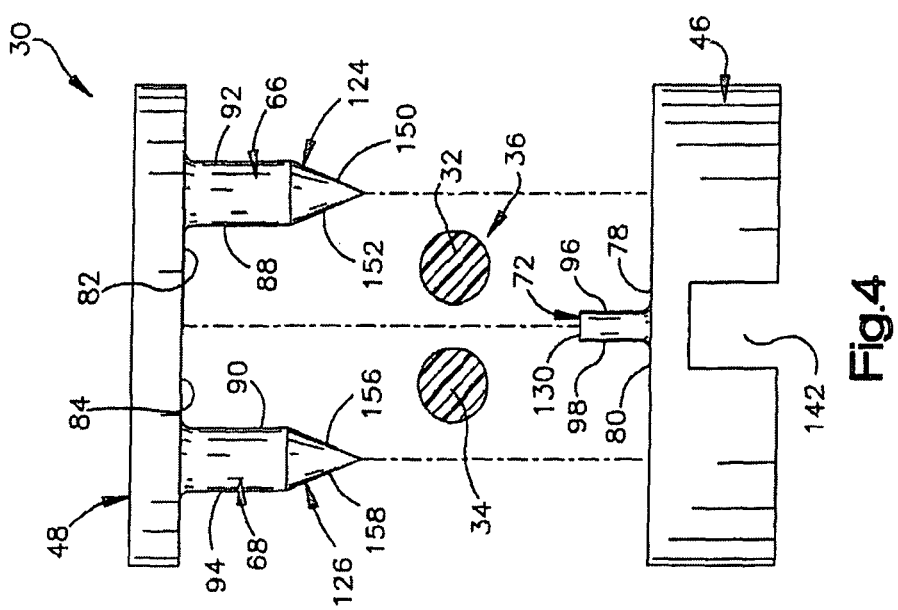

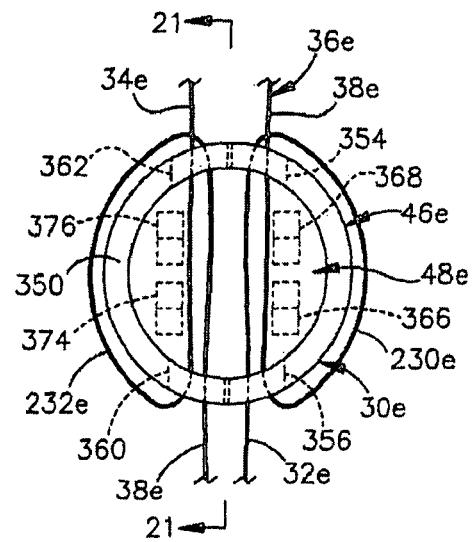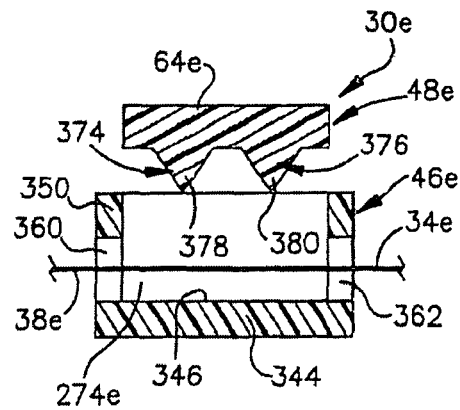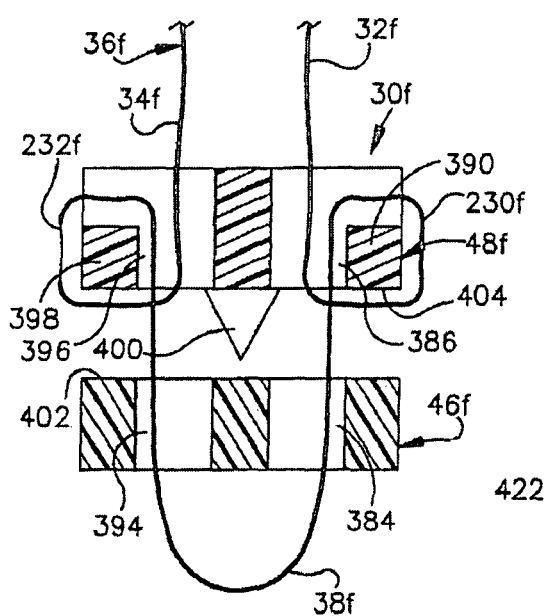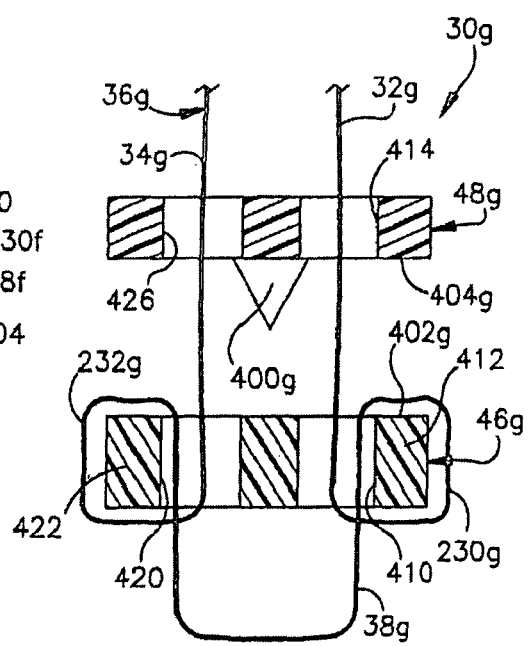

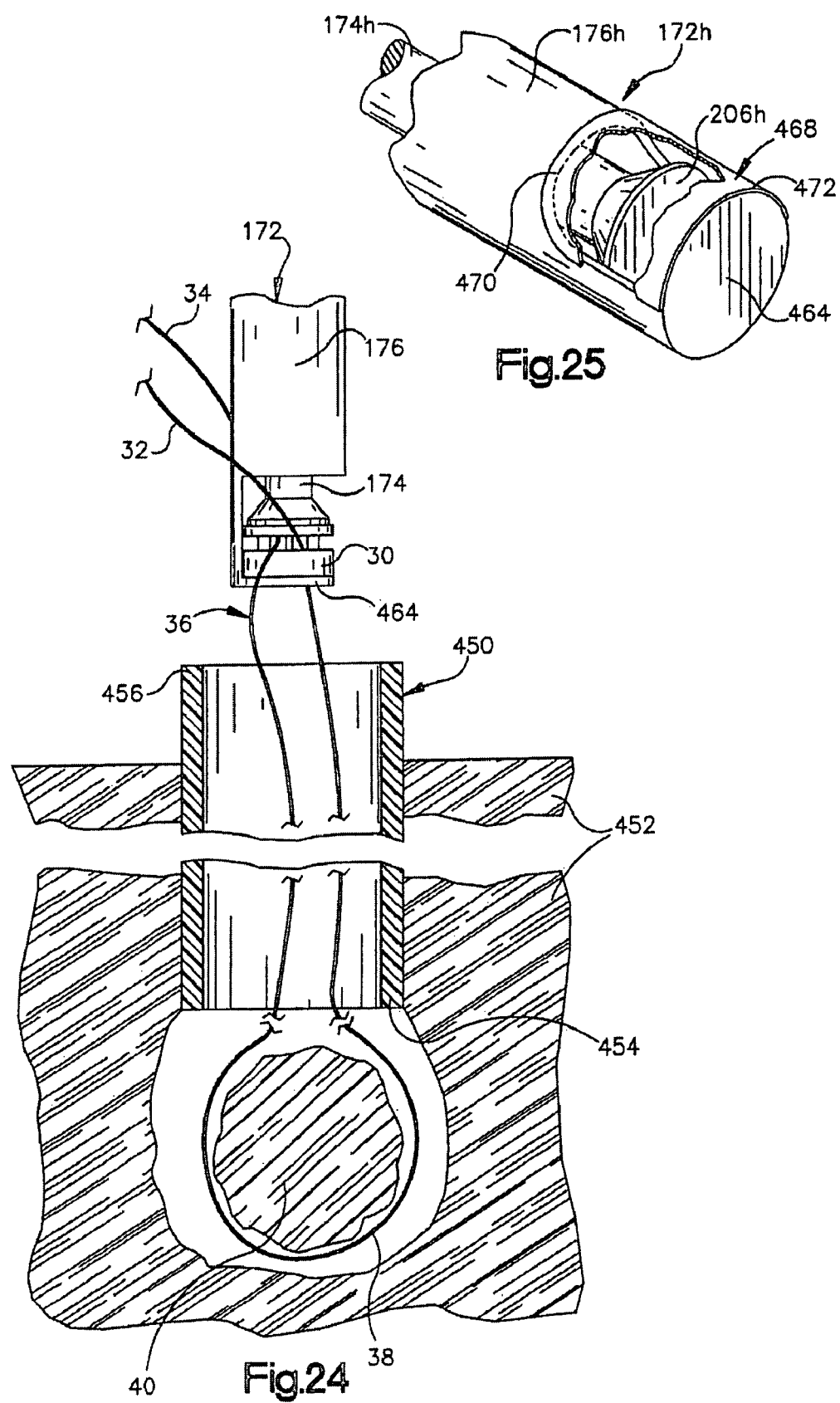

METHOD FOR JOINING IMPLANTS

CROSS-REFERENCE TO RELATED APPLICATIONS

This application is a continuation of U.S. patent application Ser. No. 11/465,199 filed on Aug. 17, 2006 now U.S. Pat. No. 7,854,750, which in turn is a continuation of U.S. patent application Ser. No. 10/228,855 filed on Aug. 27, 2002 (now U.S. Pat. No. 7,094,251). Priority to both U.S. patent application Ser. Nos. 11/465,199 and 10/228,855 is claimed under 35 U.S.C. §120.

BACKGROUND

The present invention relates to a new and improved apparatus and method which are used to secure a suture relative to body tissue.

It has previously been suggested that a retainer may be connected with a suture by applying energy to the retainer. The energy effects a bonding of one portion of the retainer to another portion of the retainer. It has previously been suggested that a retainer could be connected with a suture in the manner disclosed in Japanese laid-open Patent Application No. 8-140,982 and in U.S. Pat. Nos. 6,010,525; 6,174,324; and 6,368,343.

SUMMARY OF THE INVENTION

The present invention relates to a new and improved apparatus and method for use in securing a suture. The suture is positioned relative to sections of an improved retainer. The sections of the retainer are interconnected when the retainer has been positioned relative to a patient's body tissue. The sections of the retainer may be bonded together by the application of energy to the retainer by an improved applicator assembly.

The improved retainer may have one or more projections which engage one or more recesses to position the sections of the retainer relative to each other. An interference fit may be provided between one or more projections and one or more recesses to hold the sections of the retainer in a desired spatial relationship. The projections may have surfaces which at least partially define one or more passages and guide movement of one or more portions of the suture relative to the retainer. In addition, the surfaces on the projections may function to position the suture relative to the retainer.

The improved applicator assembly may be used to apply energy to the retainer. Energy applied to the retainer may effect bonding of end portions of the projections to bottom portions of recesses in the retainer. The end portions of the projections may function as energy directors which concentrate energy. If desired, one or more loops may be formed in the suture around one or more of the projections.

The applicator assembly may grip the retainer with a predetermined force. While the applicator assembly grips the retainer, the applicator assembly may be utilized to slide the retainer along the suture to position the retainer relative to body tissue. While the applicator assembly is gripping the retainer, the applicator assembly may apply energy to the retainer to effect bonding of sections of the retainer together. The applicator assembly may be used to move the retainer into a cannula to engage tissue in a patient's body.

The present invention includes a plurality of different features which may be utilized in combination with each other or separately. The various features of the invention may be used in combination with features of the prior art. For example, the improved retainer may be used with the improved applicator assembly or with a prior art applicator assembly. As another example, the improved applicator assembly may be used with the improved retainer or a prior art retainer. As still another example, the retainer may be moved through a cannula to a desired position relative to body tissue or may be positioned relative to the body tissue without being moved through a cannula.

BRIEF DESCRIPTION OF THE DRAWINGS

The foregoing and other features of the invention will become more apparent upon consideration of the following description taken in connection with the accompanying drawings wherein:

FIG. 1. is a fragmentary schematic illustration depicting the manner in which a suture and an improved retainer are positioned relative to body tissue;

FIG. 2. is an enlarged schematic pictorial illustration of the retainer of FIG. 1;

FIG. 3. is an exploded schematic pictorial illustration depicting the construction of a base section and cover section of the retainer of FIGS. 1 and 2;

FIG. 4. is an exploded schematic pictorial illustration, further illustrating the construction of the base and cover sections of the retainer;

FIG. 5. is an exploded schematic pictorial illustration, further illustrating the construction of the base and cover sections of the retainer;

FIG. 6. is an exploded schematic pictorial illustration further illustrating the construction of the base and cover sections of the retainer;

FIG. 20. is a schematic plan view of another embodiment of the retainer;

FIG. 21. is a schematic sectional view, taken generally along the line 21-21 of FIG. 20, further illustrating the construction of the retainer;

FIG. 22. is a schematic sectional view of another embodiment of the retainer;

FIG. 23. is a schematic sectional view of another embodiment of the retainer;

FIG. 24. is a fragmentary schematic illustration depicting the manner in which the applicator assembly of FIGS. 9-12 may be utilized to move the retainer of FIGS. 1-8 and 13-23 into a cannula; and FIG. 25. is a fragmentary schematic illustration, generally similar to FIG. 12, depicting the manner in which a shield may be provided on the distal portion of the applicator assembly of FIGS. 9-12.

DESCRIPTION OF SPECIFIC PREFERRED EMBODIMENTS OF THE INVENTION

Suture Retainer

Figure 7:
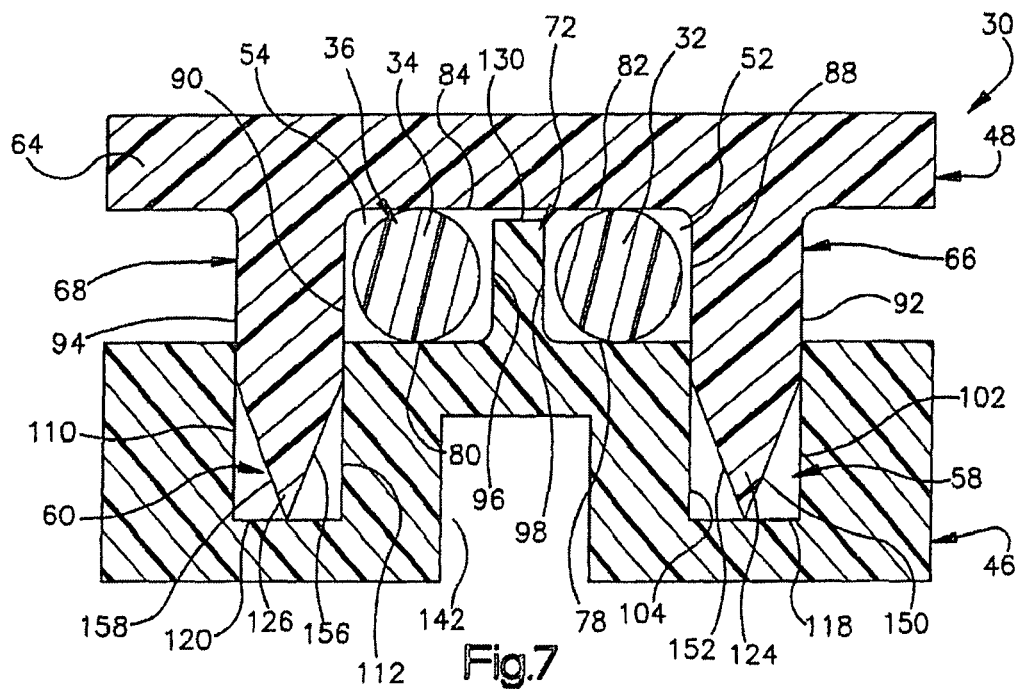
FIG. 7. is a schematic sectional view depicting the relationship between the base and cover sections of the retainer of FIGS. 1-6 with portions of the suture disposed in passages in the retainer.

An improved retainer 30 is utilized to fixedly interconnect opposite portions 32 and 34 of a suture 36. The portions 32 and 34 of the suture 36 extend in opposite directions through the retainer 30. An intermediate portion 38 of the suture extends between the portions 32 and 34 and extends around body tissue 40 to the retainer 30. It should be understood that the suture 36 and retainer 30 could be connected with each other and/or the body tissue 40 in a manner which is different than the specific manner illustrated in FIG. 1. For example, the portions 32 and 34 of the suture 36 may extend in the same direction from the retainer 30.

It is contemplated that the suture 36 and retainer 30 may be utilized to secure body tissue 40 in many different ways. For example, the suture 36 and retainer 30 may be utilized to secure one piece of body tissue to another piece of body tissue. The suture 36 and retainer 30 may be utilized to secure soft body tissue to hard body tissue (bone). The suture 36 and retainer 30 may be utilized to connect hard body tissue to hard body tissue in the manner disclosed in U.S. Pat. No. 6,238,395. The suture 36 and retainer 30 may be disposed entirely within a patient's body or may engage a surface area on the patient's body.

It is contemplated that the suture 36 can be constructed of a single filament or of a plurality of filaments. The suture 36 may be formed of biodegradable or nonbiodegradable material. Similarly, the retainer 30 may be formed of biodegradable or nonbiodegradable material.

It is believed that it may be desired to form the retainer 30 from Poly-L-Lactic Acid (PLLA) or other resorbable polymer. Although it is believed that it may be desired to form the retainer 30 and suture 36 of the same material, the retainer and suture may be formed of different materials. For example, the suture 36 and retainer 30 may both be formed of a biodegradable material. Alternatively, one of the suture 36 and retainer 30 may be formed of a biodegradable material and the other one formed of a nonbiodegradable material.

It is contemplated that the suture 36 and retainer 30 may be positioned relative to the body tissue 40 using laproscopic or arthroscopic surgical procedures. The retainer 30 and suture 36 may be moved into a patient's body through a cannula. Fiber optics may be used in association with the cannula to facilitate positioning of the suture 36 and retainer 30. The cannula may have any one of the constructions disclosed in U.S. Pat. Nos. 6,338,730 and 6,358,266. The positioning of the retainer 30 and suture 36 using endoscopic surgical procedures may be preferred in order to minimize the size of an incision in a patient's body. Of course, the retainer 30 and suture 36 may be used with an open incision which is relatively large.

Regardless of whether the retainer 30 and suture 36 are positioned in a patient's body using open or minimally invasive surgical techniques, it is contemplated that it may be desired to tension the suture 36 with a predetermined force. A predetermined tension is applied to the suture 36 by pulling the portions 32 and 34 of the suture from the retainer 30 with a predetermined force. The suture 36 is tensioned with a force which is a function of the size and strength of the suture.

The manner in which the suture 36 is tensioned with a predetermined force may be the same as is disclosed in U.S. Pat. No. 6,159,234 or in U.S. patent application Ser. No. 09/556,458 filed May 3, 2000 by Peter M. Bonutti and entitled Method And Apparatus For Securing Tissue. The suture 36 is tensioned with a predetermined force by pulling the portions 32 and 34 of the suture before securing the retainer 30 to the suture to hold the suture. When the retainer 30 has been secured to the suture 36 to hold the suture, the retainer grips the portions 32 and 34 of the suture 36 to maintain a tension, corresponding to the predetermined force, in the suture.

It is contemplated that a robotic mechanism may be utilized to position the retainer 30 and/or suture 36 relative to the body tissue. An imaging device may be utilized in association with the robotic mechanism to facilitate positioning of the retainer 30 and suture 36 relative to the body tissue. The robotic mechanism and/or imaging device may have any one of the constructions and be used in any one of the ways disclosed in U.S. patent application Ser. No. 10/102,413 filed Mar. 20, 2002 by Peter M. Bonutti and entitled Methods of Securing Body Tissue. During the surgery, the patient may be covered by a drapery system which is connected with a surgeon so as to maintain a sterile field between the surgeon and the patient in the manner disclosed in U.S. patent application Ser. No. 09/941,185 filed Aug. 28, 2001 by Peter M. Bonutti and entitled Method of Performing Surgery. Of course, any desired sterile drapery system may be provided to cover the patient.

In order to minimize the size of an incision in the patient, it is contemplated that minimally invasive surgical techniques disclosed in the aforementioned U.S. patent application Ser. No. 09/941,185 filed Aug. 28, 2001 by Peter M. Bonutti and entitled Method of Performing Surgery may be utilized. It is believed that the utilization of minimally invasive surgical techniques may be particularly advantageous when used in association with a robotic mechanism and/or imaging apparatus in the manner disclosed in U.S. patent Ser. No. 10/102,413 filed Mar. 20, 2002 by Peter M. Bonutti. It is contemplated that a magnetic suturing system having a construction similar to that in U.S. patent application Ser. No. 10/005,652 filed by Peter M. Bonutti on Dec. 3, 2001 and entitled Magnetic Suturing System and Method may be used to position the suture 36.

The retainer 30 includes a lower or base section 46 (FIGS. 2 and 3) and an upper or cover section 48. The portions 32 and 34 of the suture 36 extend through passages 52 and 54 (FIGS. 2 and 7) formed between the upper and lower sections 46 and 48 of the retainer 30. The passages 52 and 54 have a cross sectional area which is slightly greater than the cross sectional area of the suture 36 (FIG. 7). Therefore, the portions 32 and 34 of the suture 36 can be readily pulled through the passages 52 and 54 when the retainer 30 is in the initial or undeformed condition illustrated in FIG. 7. It should be understood that the passages 52 and 54 could have a configuration other than the configuration illustrated in FIG. 7.

Figure 8:
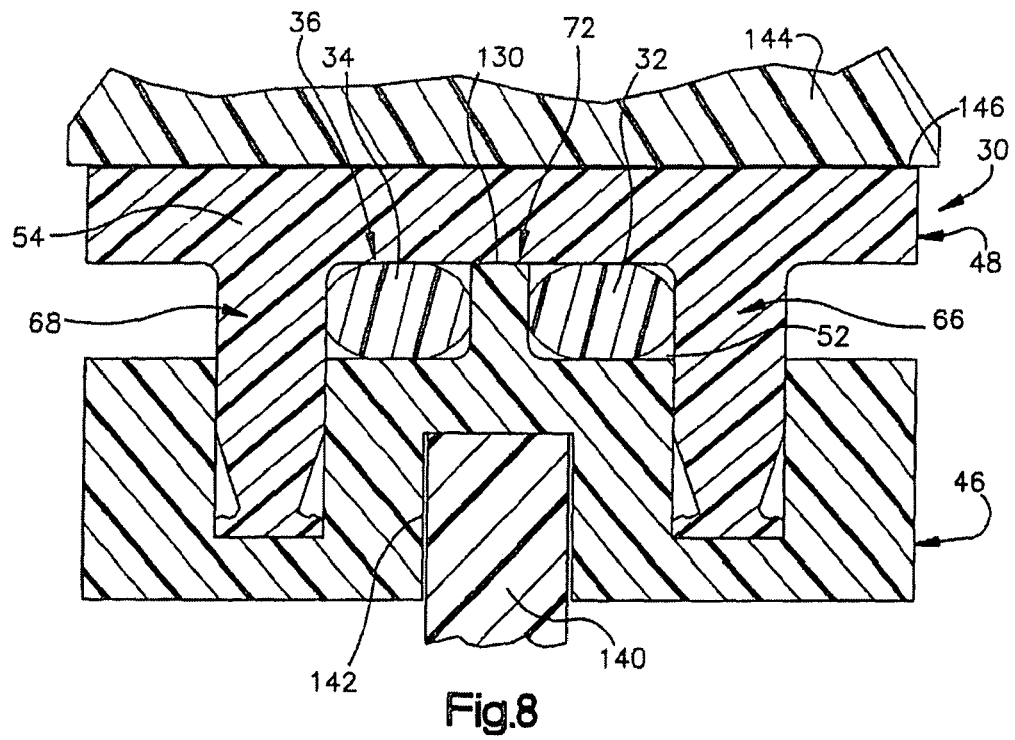
FIG. 8. is a schematic fragmentary sectional view, generally similar to FIG. 7, depicting the manner in which end portions of projections on the cover section of the retainer are bonded to bottom portions of recesses in the base section of the retainer.

Once the suture 36 has been tensioned with a desired force, the retainer 30 is plastically deformed in the manner illustrated schematically in FIG. 8. This results in the portions 32 and 34 of the suture 36 being securely gripped between the lower and upper sections 46 and 48 of the retainer 30. The portions 32 and 34 of the suture 36 are gripped with a clamping action which holds them against movement relative to each other and to the retainer 30. This results in the desired tension being maintained in the suture 36.

The lower section 46 of the retainer 30 includes a right (as viewed in FIG. 3) recess 58 and a left recess 60. The right and left recesses 58 and 60 have the same configuration and are disposed the same distance from a central axis of the circular lower section 46 of the retainer 30. Although the recesses 58 and 60 could have many different configurations, the illustrated recesses have elongated configurations with parallel longitudinal central axes which extend perpendicular to the central axis of the circular lower section 46.

The upper section 48 has a circular body 64 from which right (as viewed in FIG. 3) and left projections 66 and 68 extend. The right and left projections 66 and 68 have the same cross sectional configuration which corresponds to the cross sectional configuration of the recesses 58 and 60 (FIGS. 4, 5, 6, and 7). The projections 66 and 68 have an elongated configuration with parallel longitudinal central axes which extend perpendicular the central axis of the circular body 64 of the upper section 48 of the retainer 30. The projections 66 and 68 are disposed the same distance from a central axis of the upper section 48. It is contemplated that the projections 66 and 68 could have a configuration which is different than the specific configuration illustrated in FIGS. 4-7.

A center projection 72 is disposed on the lower section 46 of the retainer 30 at a location midway between the right and left recesses 58 and 60 (FIGS. 3, 4 and 7). The left and right projections 66 and 68 on the upper section 48 of the retainer 30 are telescopically received in the right and left recesses 58 and 60 in the lower section 46 of the retainer 30 (FIGS. 2, 3, and 7). This results in the upper section 38 of the retainer being positioned in a coaxial relationship with the lower section 36 of the retainer. The center projection 72 is disposed midway between the right and left projections 66 and 68 when they engage the right and left recesses 58 and 60. The right and left recesses 58 and 60 cooperate with the right and left projections 66 and 68 to orient the upper section of the retainer 48 with the longitudinal axes of the right and left projections 66 and 68 extending parallel to the longitudinal axis of the center section 72.

When the right and left projections 66 and 68 are disposed in the right and left recesses 58 and 60 (FIG. 7), the center projection 72 cooperates with the right and left projections to partially form the passages 52 and 54. The bottom (as viewed in FIG. 7) of the passage 52 is formed by a gripper surface area 78. The bottom of the passage 54 is formed by a gripper surface area 80.

The gripper surface areas 78 and 80 on the lower section 46 face and are parallel to gripper surface areas 82 and 84 (FIG. 7) on the upper section 48. The gripper surface areas 78, 80, 82 and 84 cooperate with the projections 66, 68 and 72 to define the parallel passages 52 and 54. The gripper surface areas 78, 80, 82 and 84 may be roughened or knurled to enhance their ability to grip the suture 36.

The right and left projections 66 and 68 have flat parallel longitudinally extending inner side surfaces 88 and 90 (FIGS. 4 and 7). The inner side surfaces 88 and 90 on the projections 66 and 68 extend perpendicular to the gripper surface areas 82 and 84 on the circular body 64 of the upper section 48 of the retainer 30. In addition, the right and left projections 68 and 70 have outer side surfaces 92 and 94 which extend parallel to the inner side surfaces 88 and 90.

The center projection 72 has parallel right and left side surfaces 96 and 98 which extend perpendicular to the gripper surface areas 78 and 80 on the lower section 46 (FIG. 4). When the right and left projections 66 and 68 on the circular body 64 of the upper section 48 of the retainer 30 are disposed in the right and left recesses 58 and 60 on the lower section 46 (FIG. 7), the right and left side surfaces 96 and 98 on the center projection 72 extend parallel to the inner side surfaces 88 and 90 on the right and left projections 66 and 68.

The passages 52 and 54 through the retainer 30 are formed by flat surfaces on the lower and upper sections 46 and 48 of the retainer. The flat side surfaces which form the parallel passages 52 and 54 are effective to guide a leading end of a portion of a suture 36 as the suture is inserted into the passage. Thus, the leading end of the portion 32 of the suture is directed by the side surfaces 78, 88, 82, and 98 (FIG. 7) formed on the lower section 46, right projection 66, body 64 and center projection 72 respectively. Similarly, the leading end of the portion 34 of the suture 36 is directed by the side surfaces 80, 90, 84 and 96 formed on the lower section 46, left projection 68, body 64 and center projection 72. By forming the passages 52 and 54 with elongated side surfaces, insertion of the portions 32 and 34 of the suture 36 into the passages is facilitated. This is because once a portion 32 or 34 of the suture 36 has been inserted into one of the passages 52 or 54, the side surfaces of the passage maintain the leading end of the suture in a desired relationship with the passage as the suture continues to be moved into the passage.

The center projection 72 is effective to position the portions 32 and 34 of the suture 36 so that they are disposed on opposite sides of and equal distances from a central axis of the retainer 30. This results in off setting movements being applied to the retainer 30 by forces transmitted to the retainer from the portions 32 and 34 of the suture 36. Therefore, there is little or no tendency for the retainer 30 to rotate or flip relative to the body tissue 40.

The right and left projections 66 and 68 on the upper section 48 of the retainer 30 are disposed in the recesses 58 and 60 in the lower section 46 of the retainer 78 (FIG. 7) during insertion of the portions 32 and 34 of the suture 36 into the passages 52 and 54 in the retainer 30. To hold the projections 66 and 68 in the recesses 58 and 60, there is an interference fit between the projections and the recesses. Thus, the distance between an outer side surface 102 of the right recess 58 (FIG. 7) and an inner side surface 104 of the right recess is slightly less than the distance between the outer side surface 92 and inner side surface 88 on the right projection 66. The resulting interference between the right projection 66 and the right recess 58 is effective to hold the right projection in the right recess.

Similarly, the left recess 60 has parallel outer and inner side surfaces 110 and 112. The outer and inner side surfaces 110 and 112 of the left recess 60 are spaced apart by distance which is slightly less than the distance between the outer side surface 94 and inner side surface 90 on the left projection 68. When the left projection 68 is pressed into the left recess 60, the resulting interference between the side surfaces 90 and 94 on the projection 68 and the side surfaces 110 and 112 on the recess 60 hold the left projection in the left recess. The side surfaces 102, 104, 110 and 112 on the recesses 58 and 60 extend parallel to the side surfaces 96 and 98 on the center projection 72 and perpendicular to the gripper surface areas 78 and 80 on the lower section 46.

The interference fit between the projections 66 and 68 on the upper section 48 of the retainer with the recesses 58 and 60 in the lower section 46 of the retainer holds the two sections of the retainer against movement relative to each other during insertion of the portions 32 and 34 of the suture 36 into the passages 52 and 54. However, it is contemplated that the upper section 48 and lower section 46 of the retainer 30 may be held against movement relative to each other by means other than an interference fit. For example, latch surfaces on the projections 66 and 68 may engage latch surfaces formed on the sides of the recesses 58 and 60. These latch surfaces may have a generally wedge shaped configuration. Alternatively, a pin may extend through at least a portion of the lower section 46 of the retainer and the projections 66 and 68 on the upper section 48 of the retainer to hold the upper section against movement relative to the lower section.

The lower section 46 and upper section 48 of the retainer 30 are formed as two separate pieces. However, it is contemplated that the lower and upper sections 46 and 48 of the retainer 30 could be formed as one piece. If this is done, relatively weak connectors may be provided between the projections 66 and 68 and the base section 46 to hold the base and upper sections 46 and 48 in a desired spatial relationship with each other during insertion of the portions 32 and 34 of the suture 36 into the passages 52 and 54. The weak connectors may be broken to enable the portions 32 and 34 of the suture 36 to be gripped between the retainer sections 46 and 48. Alternatively, a flexible strap may be formed between the base section 46 and upper section 48. By deflecting the strap, the projections 66 and 68 may be inserted into the recesses 58 and 60.

When the right and left projections 66 and 68 are telescopically inserted into the right recess 58 and left recess 60, the leading or lower (as viewed in FIG. 7) end portions of the projections engage flat bottom surfaces 118 and 120 of the recesses 58 and 60 (FIG. 7). The flat bottom surfaces 118 and 120 extend parallel to the gripper surface areas 78 and 80 on the lower section 46 and perpendicular to the side surfaces 102, 104, 110 and 112 of the recesses 58 and 60. Engagement of end portions 124 and 126 of the projections 66 and 68 with the bottom surfaces 118 and 120 of the recesses 58 and 60 positions the lower and upper sections 46 and 48 of the retainer relative to each other and determines the size of the passages 52 and 54. This results in the passages 52 and 54 being sized so as to have a cross sectional area which is slightly greater than the cross sectional area of the portions 32 and 34 of the suture 36 to enable the suture to be readily inserted into the passages.

The center projection 72 has a flat upper side surface 130 which extends parallel to the gripper surfaces 78, 80, 82 and 84. The upper side surface 130 on the center projection 72 is spaced from the upper section 48 when the end portions 124 and 126 of the projections 66 and 68 are in engagement with the bottom surfaces 118 and 120 of the recesses 58 and 60. However, if desired, the center projection 72 may be disposed in engagement with the upper section 48 when the end portions 124 and 126 of the projections 66 and 68 are in engagement with the bottom surfaces 118 and 120 of the recesses 58 and 60.

When the end portions 124 and 126 of the projections 66 and 68 are in engagement with the bottom surfaces 118 and 120 of the recesses 58 and 60, the portions 32 and 34 of the suture 36 can be freely moved in the passages 52 and 54 to enable the retainer 60 to be slid along the suture 36 to a desired position relative to the body tissue 40. The retainer 30 may be slid along the suture 36 under the influence of force manually applied against the retainer or under the influence of force applied against the retainer by a surgical instrument, such as forceps. As this occurs, the intermediate portion 38 (FIG. 1) of the suture is tightened around the body tissue with a desired force.

Once the retainer 30 has been positioned in a desired location relative to the body tissue 40 and the suture 36 tensioned with a predetermined force, the retainer is plastically deformed from the initial condition illustrated in FIG. 7 to the condition illustrated in FIG. 8. Plastic deformation of the retainer 30 results in the size of the passages 52 and 54 being decreased. In addition, the upper side 130 on the center projection 72 moves into engagement with the upper section 48 of the retainer 30. Engagement of the center projection 72 with the upper section 48 of the retainer 30 tends to limit the extent to which the lower and upper section 46 and 48 of the retainer are pressed together to thereby limit plastic deformation of the retainer 30.

If the retainer 30 is constructed so that the center projection 72 engages the upper section 48 of the retainer when the end portions 124 and 126 of the projections 66 and 68 are in engagement with the bottom surface areas 118 and 120 of the recesses 58 and 60, the center projection would also be deformed when the retainer is plastically deformed from the initial condition of FIG. 7 to the condition of FIG. 8. With this construction of the retainer 30, the center projection 72 would be deformed to the same extent as the projections 66 and 68. Therefore, the center projection 72 may be formed with an upper end portion which has the same configuration as the lower end portions 124 and 126 of the projections 66 and 68.

To plastically deform and interconnect the lower and upper sections 46 and 48 of the retainer 30, a member 140 (FIG. 8) is moved into a groove 142 in the lower section 46. In addition, a second member 144 engages a flat outer side surface 146 on the upper section 48 of the retainer 30. The lower and upper sections 46 and 48 of the retainer 30 are firmly pressed together by force transmitted between the members 140 and 144 through the retainer. While the lower and upper sections 46 and 48 of the retainer 30 are gripped between the members 140 and 144 with a clamping action, energy is transmitted from the member 144 to the retainer 30.

The energy applied to the retainer 30 is effective to heat the end portions 124 and 126 of the projections 66 and 68 into a transition temperature range for the polymeric material of the projections. Force applied against the retainer 30 by the members 140 and 144 (FIG. 8) causes the heat softened material of the projections 66 and 68 to flow in the recesses 58 and 60. To a lesser extent, material of the lower section 46 is heated and also flows in the recesses 58 and 60.

As this occurs, the heated material of the projections 66 and 68 may be forced upward toward the portions 32 and 34 of the suture 36. The heated material tends to bond to the portions 32 and 34 of the suture 36. it should be understood that the extent of deformation and flow of the heat softened material of the projections 66 and 68 may be and probably will be greater than the extent illustrated schematically in FIG. 8.

If the retainer 30 is constructed so that the center projection 72 is deformed to the same extent as the projections 66 and 68, heat softened material of the center projection would flow into the passages 52 and 54. If the upper section 48 of the retainer 30 has the construction shown in FIG. 4, the upper end portion of the center projection would engage the flat lower side surface of the body 64. However, the upper section 48 of the retainer 30 may be formed with a recess to receive the upper end portion of the center projection 72. This recess may have the same configuration as the recesses 58 and 60 in the lower section 46 of the retainer 30.

If desired, the retainer 30 may be constructed with the center projection 72 extending from the upper section 48 of the retainer. If this is done, the center projection 72 from the upper section 48 of the retainer may have the same configuration as the illustrated configuration of the center projection in FIGS. 4 and 5. A recess may be provided in the lower section 46 to receive a portion of a center projection from the upper section 48 of the retainer 30.

As the heated material of the projections 66 and 68 is caused to flow in the recess 58 and 60, the size of the passages 52 and 54 is decreased. This results in the portions 32 and 34 of the suture 36 being firmly clamped between the gripper surface areas 78 and 80 on the lower section 46 and the gripper surface areas 82 and 84 on the upper section 48 of the retainer 30. The force applied to the portions 32 and 34 of the suture 36 by the gripper surface areas 78, 80, 82 and 84 on the lower and upper sections 46 and 48 of the retainer 30 is effective to deform the suture from the circular cross sectional configuration illustrated in FIG. 7 to a generally oval cross sectional configuration illustrated schematically in FIG. 8. Although the illustrated suture 36 is a monofilament, it is contemplated that the suture could be formed by a plurality of filaments which are braided or twisted together.

The energy which is applied to the retainer 30 by the member 144 may be thermal energy, vibratory energy, or light energy. The energy may be transmitted by radio frequency waves, ultrasonic waves, heat waves, or light waves. The energy may be vibratory ultrasonic or radio frequency energy. Rather than positioning the member 140 in the groove 142 in the lower section 46 of the retainer 30, the groove 142 may be omitted and a flat member, similar to the member 144, may be pressed against the lower section 46 of the retainer 30. Energy may be transmitted to the retainer through either the member 140 or the member 144 or both of the members 140 and 144.

In the embodiment of the invention illustrated in FIG. 8, the portions 32 and 34 of the suture 36 are clamped between the lower section 46 and upper section 48 of the retainer 30. The clamping force applied against the portions 32 and 34 of the suture 36 by the retainer 30, holds the retainer and the portions of the suture against relative movement. This results in the suture 36 and retainer 30 being securely interconnected.

There is some bonding of material of the retainer to the portions 32 and 34 of the suture 36 to further interconnect suture and the retainer. However, the amount of force and energy transmitted from the member 140 or both of the members 140 and 144 to the retainer 30 is sufficient to effect a plastic deformation of the material of the retainer without excessive plastic deformation of the material of the suture 36. By avoiding excessive deformation of the material of the suture 36, weakening of the suture is avoided. Thus, once the plastic deformation of the retainer 30 has been effected by the transmission of force and energy to the retainer, the lower and upper sections 46 and 48 of the retainer are fixedly interconnected with the suture 36 without significantly weakening of the suture.

The end portions 124 and 126 of the projections 66 and 68 have a pointed configuration. Thus, the end portion 124 of the projection 66 includes a flat side surface area 150 which intersects a flat side surface area 152 at a linear point or peak. Therefore, there is line contact between the end portion 124 of the right projection 66 and the flat bottom surface 118 of the right recess 58. Similarly, the end portion 126 of the left projection 68 has a flat side surface 156 which intersects a flat side surface 158 at a linear point or peak on the end portion 126 of the left projection 68. This results in line contact between the pointed end portion of the left projection 68 and the flat bottom surface 120 of the left recess 60. However, the end portions 124 and 126 of the projections 66 and 68 may have a conical configuration if desired.

By forming the end portions 124 and 126 of the right and left projections 66 and 68 with a pointed configuration, the end portions of the projections are effective to function as energy directors for ultrasonic vibratory energy. The pointed end portions 124 and 126 of the right and left projections 66 and 68 are effective to direct ultrasonic vibratory energy transmitted from the member 144 to the ends of the projections and to the bottom surfaces 118 and 120 of the recesses 58 and 60. The pointed configuration of the end portions 124 and 126 of the projections 66 and 68 concentrates the energy and facilitates melting of the material of the projections. To a lesser extent, the material of the lower section 46 of the retainer 30 is melted adjacent to the bottom surfaces 118 and 120. This results in a secure bonding and interconnection between the lower and upper sections 46 and 48 of the retainer 30.

Applicator Assembly

An improved applicator assembly 172 (FIGS. 9-12) is utilized to grip the retainer 30 with a constant predetermined force, to move the retainer 30 along the suture 36 to a desired position relative to the body tissue 40, and to transmit energy to the retainer 30. The applicator assembly 172 may be used to perform any one or more of foregoing functions rather than all of the functions.

The applicator assembly 172 includes a rigid energy transmission member 174 (FIG. 9) which corresponds to the member 144 in FIG. 8. A rigid tubular force transmitting member 176 extends around and is coaxial with the cylindrical energy transmission member 174. The cylindrical force transmitting member 176 corresponds to the member 140 in FIG. 8.

A biasing assembly 178 continuously urges the force transmitting member 176 toward the left (as viewed in FIG. 9) with a constant predetermined force. The illustrated embodiment of the biasing assembly 178 includes a helical spring 180 which is disposed between an annular flange 182 on a reaction member 184 and an annular piston 186. The annular piston 186 is fixedly connected to a housing 188. The housing 188 is connected to the tubular force transmitting member 176. The reaction member 184 is fixedly connected to a manually engagable handle 194.

A trigger 198 is pivotally connected with the handle 194. The trigger 198 is manually pivotal in a clockwise direction (as viewed in FIGS. 9 and 11). Clockwise pivotal movement of the trigger 198 transmits force through a yoke 200. The force transmitted through the yoke 200 moves the housing 188 toward the right (as viewed in FIGS. 9 and 11). This rightward movement of the housing 188 moves a flange 204 on the right (as viewed in FIGS. 9 and 12) or distal end of the tubular force transmitting member 176 away from a circular end surface 206 on the energy transmission member 174.

The rightward (as viewed in FIGS. 9 and 12) movement of the force transmitting member 176 relative to the energy transmission member 174 increases space between the flange 204 and end surface 206 on the energy transmission member 174. Increasing the space between the flange 204 and the end surface 206 enables the retainer 30 to be positioned between the flange 204 and the end surface 206 with the portions 32 and 34 of the suture 36 extending through the passages 52 and 54 in the retainer 30 in the manner illustrated in FIG. 7.

When the retainer 30 is positioned in the gap between the end surface 206 (FIGS. 9 and 12) on the energy transmission member 174 and the flange 204 connected with the force transmitting member 176, the flange 204 is positioned in the groove 142 in the retainer 30 in the same manner as in which the member 140 is illustrated as engaging the groove 142 in FIG. 8. The end surface 206 (FIGS. 9 and 12) on the energy transmission member 174 is disposed in engagement with the surface 146 on the upper section 48 of the retainer 30 in the same manner as in which the member 144 (FIG. 8) engages the surface 146.

Once the retainer 30 has been positioned in the space between the flange 204 and the end surface 206 on the energy transmission member 174 (FIGS. 9 and 12), the trigger 198 is released. When the trigger 198 is released, the biasing spring 180 is effected to urge the housing 188 toward the left (as viewed in FIGS. 9 and 11). The leftward force applied by the spring 180 against the housing 188 is transmitted through the force transmitting member 176 and flange 204 to the retainer 30. This results in the retainer 30 being clamped between the flange 204 on the force transmitting member 176 and end surface 206 on the energy transmission member 174. The spring 180 is effective to apply a constant predetermined biasing force to the piston ring 186. This constant biasing force is transmitted through the housing 188 and force transmitting member 176 to the retainer 30.

Prior to the transmission of energy to the retainer 30 through the energy transmission member 174, the force applied against the retainer 30 is ineffective to cause significant plastic deformation of the material of the retainer 30. At this time, the end portions 124 and 126 (FIG. 7) of the right and left projections 66 and 68 are pressed against the bottom surfaces 118 and 120 of the recesses 58 and 60 with a constant force. The portions 32 and 34 of the suture 36 are freely movable in the passages 52 and 54.

While the retainer 30 is gripped with a predetermined constant force by the applicator assembly 172, the retainer is moved to a desired position relative to the body tissue 40. To position the retainer 30 relative to the body tissue, the surgeon holds the handle 194 of the applicator assembly 172 in one hand and tensions the portions 32 and 34 of the suture 36 with the other hand. The surgeon then manually applies force against the handle 194 to slide the retainer 30 along the tensioned portions 32 and 34 of the suture 36 toward the body tissue 40. The relatively long force transmitting member 176 and energy transmitting member 174 enable the applicator assembly 172 to move the retainer 30 through a small incision to a remote location in a patient's body as the retainer slides along the suture 36.

During performance of a surgical procedure, the suture 36 may be moved through a cannula to a location disposed within a patient's body. The suture 36 is then positioned relative to the tissue 40 at the remote location in the patient's body. However, it should be understood that the cannula may be omitted and the suture 36 moved through an open incision.

Once the suture 36 has been moved to the desired location relative to the tissue 40 in the patient's body, the portions 32 and 34 of the suture may be positioned in the passages 52 and 54 through the retainer while the retainer is disposed outside of the patient's body. Once the portions 32 and 34 of the suture 36 have been positioned in the passages 52 and 54 to the retainer 30, the retainer is gripped by the applicator assembly 172. The flange 204 on the force transmitting member 176 and end surface 206 on the energy transmission member 174 of the applicator assembly 172 are effective to apply a predetermined constant force against opposite sides of the retainer 30 to securely grip the retainer with the applicator assembly 172.

While the retainer is gripped by the applicator assembly 172, the end portions 32 and 34 of the suture are manually tensioned and the retainer is slid along the portions 32 and 34 of the suture toward the body tissue. As the retainer 30 is slid along the suture 36 toward the body tissue 40, the applicator assembly 172 moves the retainer into the patient's body. As the retainer 30 is moved into the patient's body, it is gripped with a constant predetermined force by the applicator assembly 172.

Alternatively, the retainer 30 may be gripped by the applicator assembly 172 outside of the patient's body prior to insertion of the portions 32 and 34 of the suture through the passages 52 and 54. The portions 32 and 34 of the suture 36 may then be inserted through the passages 52 and 54 in the retainer 30 while the retainer is gripped by the applicator assembly 172. If desired, insertion of the portions 32 and 34 of the suture 36 through the passages 52 and 54 in the retainer 30 may be performed with the retainer inside the patient's body.

If the applicator assembly 172 is utilized to move the retainer 30 through a cannula into the patient's body before the suture 36 is inserted into the passages 52 and 54 through the retainer, suitable instruments may be utilized to grip the portions 32 and 34 of the suture in the patient's body and to move the portions 32 and 34 of the suture through the passages 52 and 54. The instruments which engage the suture and move it through the passages 52 and 54 while the retainer 40 is gripped by the applicator assembly 172, may extend through the cannula along with the applicator assembly. Alternatively, the instruments which move the portions 32 and 34 of the suture 36 through the passages 52 and 54 may be moved into the patient's body through a cannula spaced from the cannula through which the applicator assembly 172 moves the retainer into the patient's body. In order to minimize incisions in the patient's body, it may be preferred to utilize a single cannula to accommodate movement of the applicator assembly 172, retainer 30, suture positioning instruments, and the suture 36 into the patient's body.

It is contemplated that it may be desired to position the suture 36 and retainer 30 in a patient's body with a robotic mechanism. When this is to be done, the manually engagable handle 194 and trigger 198 on the applicator assembly 172 may be eliminated. The remainder of the applicator assembly may then be connected with the robotic mechanism. A suitable motor may be provided in the robotic mechanism to move the force transmitting member 176 against the influence of the biasing spring 180. Even though the handle 194 and trigger 198 are eliminated, the retainer 30 would be gripped between the flange 204 on the force transmitting member 176 and end surface 206 on the energy transmission member 174 with a constant force.

The robotic mechanism with which the applicator assembly 172 is connected may have a plurality of adaptive arms which are effective to move the retainer 30 and other instruments in a patient's body. The robotic mechanism may be a reprogrammable, multifunctional manipulator designed to move through various program motions for the performance of selected one of a plurality of surgical procedures. The robotic mechanism may have manually operable controls which provide for interaction between a surgeon and the robotic mechanism. The robotic mechanism may have any one of many different constructions and may be operated in any one of many different manners, including those disclosed in U.S. patent application Ser. No. 10/102,413 filed Mar. 20, 2002 by Peter M. Bonutti and entitled Methods of Securing Body Tissue.

When the applicator assembly 172 is to be utilized in association with a robotic mechanism, it is believed that it may be desired to utilize a monitor or display in association with the robotic mechanism. A single imaging device or a plurality of imaging devices may be used. If a plurality of imaging devices are used, it is contemplated that stereoscopic and/or video stereoscopic viewing at a location where a surgical procedure is being performed may be accommodated by the imaging apparatus. The imaging apparatus may include a plurality of endoscopes.

A navigation system may be utilized to provide inputs to the computer to assist in the control of the robotic mechanism and the performance of a surgical procedure. The navigation system may be an optical navigation system in which end portions of navigation members are illuminated by light. The navigation members may be connected with one or more tissues in a patient's body. The tissue with which the navigation members are connected may either bone or soft tissue.

It is also contemplated that imaging devices such as a fluoroscope, and/or magnetic resonance imaging unit and/or ultrasonic imaging unit may be utilized with the robotic mechanism. If desired, endoscopes may be utilized in association with the various imaging units. The imaging units and robotic mechanisms may have a construction and cooperate with each other in the same manner as described in the aforementioned U.S. patent application Ser. No. 10/102,413 filed Mar. 20, 2002 by Peter M. Bonutti.

Once the retainer 30 has been positioned in a desired relationship with body tissue 40 and the suture 36, the portions 32 and 34 of the suture 36 are pulled with a predetermined force. This results in a predetermined tension being established in the portions 32 and 34 of the suture 36. While the predetermined tension is maintained in the suture 36, the retainer 30 is plastically deformed to connect the retainer with the portions 32 and 34 of the suture 36 and hold the portions 32 and 34 of the suture against movement relative to each other and the retainer 30. To effect plastic deformation of the retainer 30 and connection of the retainer with the suture 36, energy is transmitted from an energy source 212 (FIG. 9) through the energy transmission member 174 to the retainer 30. At this time, the retainer 30 is clamped between the flange 204 on the force transmitting member 176 and the end surface 206 on the energy transmission member 174.

In the illustrated embodiment of the applicator assembly 172, the energy source 212 is a source of ultrasonic vibratory energy at a frequency above that which can normally be detected by the human ear, that is about 16 to 20 kilohertz. Although there are a wide range of frequencies which may be utilized, it is believed that it may be desirable to use ultrasonic energy having a frequency of between 20 kilohertz and 70 kilohertz. It is believed that it may be desired to use ultrasonic vibratory energy of a frequency between 39.5 and 41 kilohertz. When a foot pedal actuated switch 214 (FIG. 9) is closed, ultrasonic vibratory energy is transmitted through the energy transmission member 174 to the retainer 30. The ultrasonic vibratory energy creates frictional heat at the pointed end portions 124 and 126 of the projections 66 and 68. The frictional heat provided by the ultrasonic vibratory energy is effective to heat material of the suture retainer 30 into its transition temperature range while the material of the suture 36 remains at a temperature below its transition temperature range. For example, the suture 36 may be formed of a material having a transition temperature range which is above 190 degrees Celsius. The suture retainer 40 may have a transition temperature range which begins at a temperature below 190 degrees Celsius.

However, it should be understood that even the entire transition temperature range for the suture 36 could be co-extensive with the transition temperature range for the retainer 30. In fact, the transition temperature range of the suture 36 could extend below the transition temperature range of the retainer 30. However, it is believed that it may be preferred to have the transition temperature range for the suture 36 above at least a portion of the transition temperature range of the retainer 30.

Ultrasonic vibratory energy is transmitted from the energy transmission member 174 to the upper section 48 of the retainer 30. The right and left projections 66 and 68 (FIG. 7) from the upper section 48 of the retainer 30 function as energy directors which direct the ultrasonic vibratory energy to the locations where the end portions 124 and 126 of the projections 66 and 68 engage the bottom surfaces 118 and 120 of the recesses 58 and 60 in the lower section 46 of the retainer 30. The pointed end portions 124 and 126 of the projections 66 and 68 concentrate the vibratory energy transmitted through the energy transmission member 174 at the locations where the projections engage the bottom surfaces 118 and 120 of the recesses 58 and 60.

The ultrasonic vibratory energy is effective to soften and make the material forming the end portions 124 and 126 of the projections 66 and 68 flowable under the influence of the constant predetermined force transmitted from the biasing spring 180 through the force transmission member 176 and flange 204 to the lower section 46 of the retainer 30. As the temperature of the end portions 124 and 126 of the projections 66 and 68 increases, the lower section 46 of the retainer 30 moves toward the upper section 48 of the retainer. This results in material which originally formed the pointed end portions 124 and 126 of the projections 66 and 68 being deflected sideways in the lower (as viewed in FIG. 7) portions of the recesses 58 and 60.

The continued application of a constant clamping force to the retainer 30 and the transmission of vibratory energy to the retainer causes the end surface 130 on the center projection 72 to move into engagement with the circular body 64 of the upper section 48. There may be a limited heating, melting and deformation of the center projection 72 as a result of engagement of the center projection with the upper section 48.

Although it is believed that it will be preferred to apply ultrasonic vibratory energy to the retainer 30, other forms of energy may be applied to the retainer if desired. For example, thermal or light (laser) energy may be applied to the retainer if desired. The energy application apparatus may be separate from the apparatus which is used to position the retainer relative to the body tissue 40 and suture 36. Thus, the retainer 30 may be positioned relative to body tissue 40 and the suture 36 manually or by using a first apparatus. Energy may then be applied to the retainer 30 using a second apparatus.

The heated, flowable material of the end portions 124 and 126 of the projections 66 and 68 may flow along the side surfaces 102, 104, 110 and 112 of the recesses 58 and 60. Some of the material of the end portions 124 and 126 of the projections 66 and 68 may engage and bond to the portions 32 and 34 of the suture 36.

At the same time, the portions 32 and 34 of the suture 36 are deflected from their original circular configuration (FIG. 7) to an oval configuration under the influence of force applied against the portions of the suture disposed between the lower section 46 and upper section 48 of the retainer 30. Although the portions 32 and 34 of the suture 36 are resiliently deflected to the configuration illustrated schematically in FIG. 8, there is minimal bonding of the material with the retainer 30 to the suture 36 and no significant loss of strength of the suture. Due to the clamping action between the flange 204 and end surface 206 on the energy transmission member 174 (FIG. 9) against the retainer 30, the overall height of the retainer is decreased. At the same time, the overall diameter of the retainer increases.

When the transmission of ultrasonic vibratory energy through the energy transmission member 174 is interrupted, the material of the retainer 30 cools and there is an ultrasonic welding of the lower section 46 of the retainer to the upper section 48 of the retainer. The bonding between the lower section 46 and upper section 48 of the retainer 30 occurs mainly between the projections 66 and 68 and the lower section 48 of the retainer. There may be some bonding of the center projection 130 to the circular body 64 of the upper section 48 of the retainer. In addition, there may be some bonding material of the lower section 46 and upper section 48 of the retainer to the portions 32 and 34 of the suture 36.

The portions 32 and 34 of the suture 36 are held against movement relative to each other and to the retainer primarily 30 by a clamping action between surfaces on the lower section 46 and surfaces on the upper section 48 of the retainer. Thus, the portions 32 and 34 of the suture 36 are securely gripped between the gripper surface areas 78 and 80 on the lower section 46 of the retainer 30 and the gripper surface areas 82 and 84 on the upper section 48 of the retainer 30. By holding the portions 32 and 34 of the suture 36 against movement relative to each other and to the retainer 30 with a clamping action, there is minimal deformation of the suture and the strength of the suture is not impaired.

Figure 9:
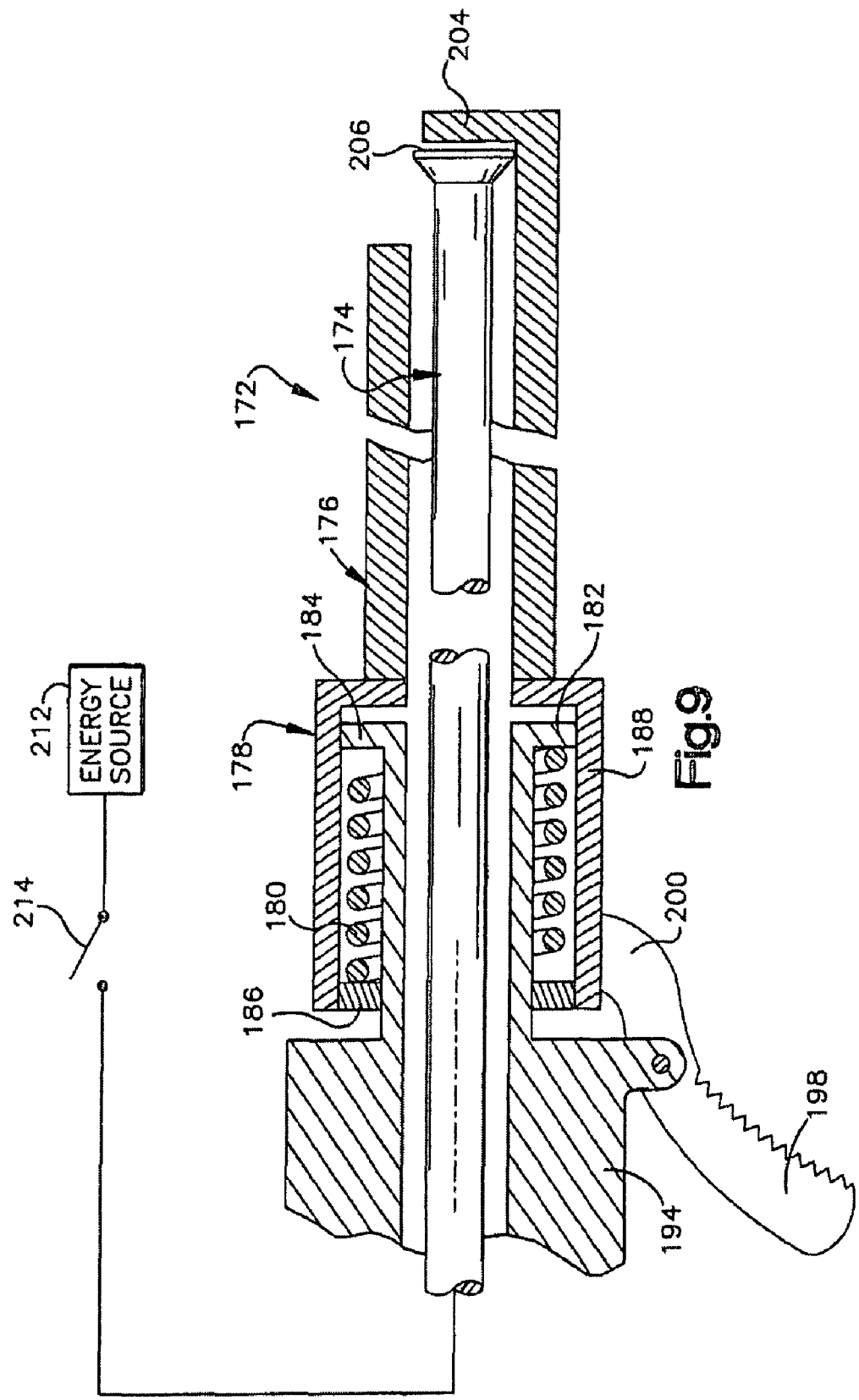
FIG. 9. is a highly schematized sectional view illustrating the construction of an improved applicator assembly which is utilized to interconnect sections of the retainer of FIGS. 1-7 in the manner illustrated schematically in FIG. 8.
Figure 10:
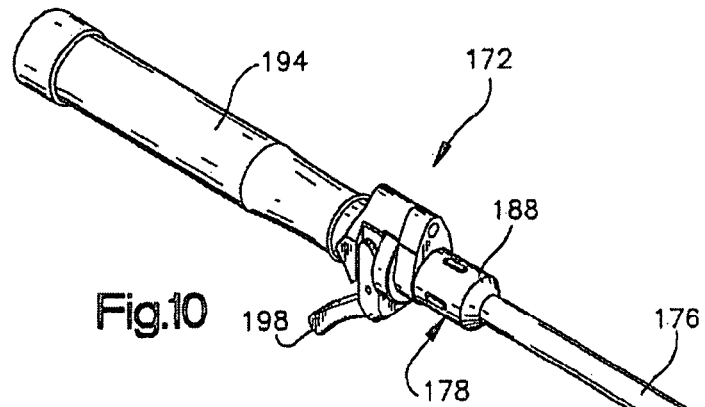
FIG. 10. is a schematic pictorial illustration of one embodiment of the applicator assembly of FIG. 9.
Figure 11:
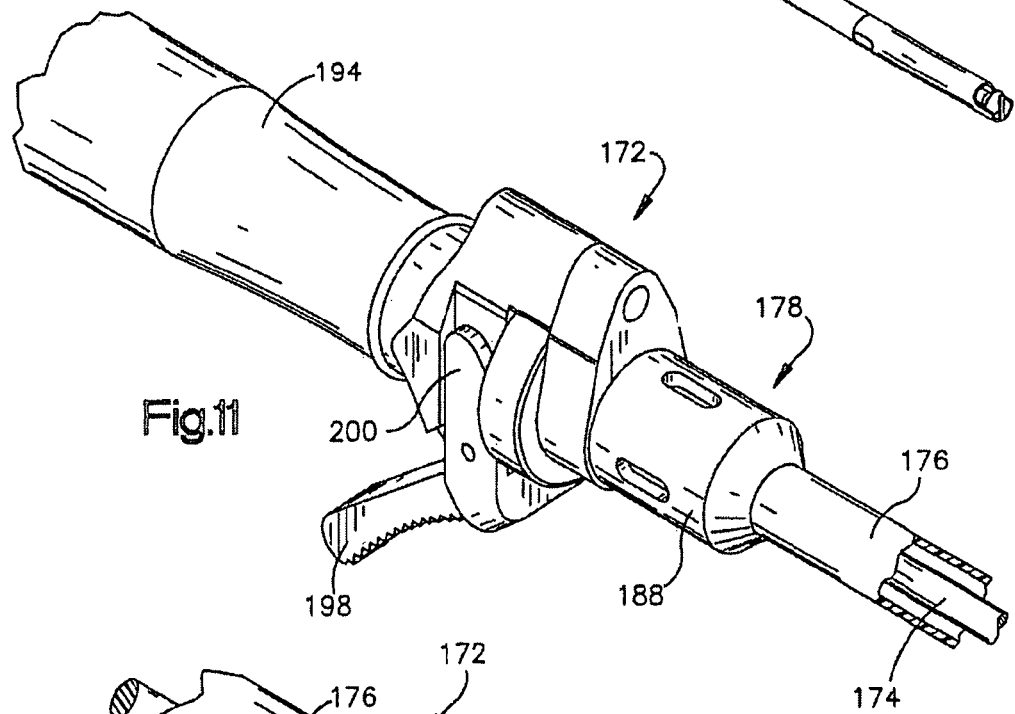
FIG. 11. is an enlarged fragmentary schematic pictorial illustration of a portion of the applicator assembly of FIG. 10, illustrating a trigger and spring housing.
Figure 12:
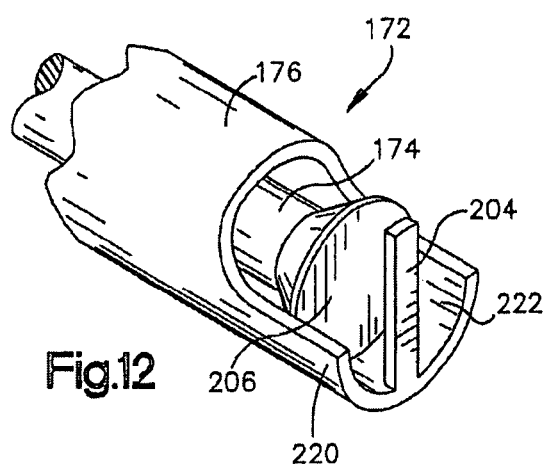
FIG. 12. is an enlarged fragmentary schematic illustration of an end portion of the applicator assembly of FIG. 10.

Although one specific preferred embodiment of the applicator assembly 172 has been illustrated in FIGS. 10-12, it is contemplated that the applicator assembly could have a different construction and/or mode of operation. For example, the applicator assembly 172 may have any one of the constructions and mode of operations disclosed in U.S. patent application Ser. No. 10/076,919 filed Feb. 15, 2002 by Peter M. Bonutti, et al and entitled Method of Using Ultrasonic Vibration to Secure Body Tissue. Although it is believed that a retainer having a construction similar to that illustrated in FIGS. 1-8 may be preferred, it is contemplated that the applicator assembly 172 of FIGS. 9-12 may be utilized with retainers having a different construction. For example, the applicator assembly 172 may be utilized in association with a retainer having any one of the constructions disclosed in the aforementioned U.S. patent application Ser. No. 10/076,919 filed Feb. 15, 2002 by Peter M. Bonutti or any one of the constructions disclosed in U.S. Pat. No. 6,010,525.

The leading end portion of the force transmitting member 176 (FIG. 12) extends part way around the end surface 206 on the energy transmission member 174. This results in the formation of a shield 220 which extends part way around the retainer 30 when the retainer 30 is clamped between the flange 204 and the end surface 206 on the energy transmission member 174. The shield 220 has an inner side surface 222 which forms a portion of a cylinder. The side surface 222 engages the cylindrical periphery of the retainer 30 to position the retainer relative to the energy transmission member 174 in a direction transverse to a longitudinal central axis of the energy transmission member.

The shield 220 is effective to at least partially block engagement of body tissue with the retainer 30 as the retainer is positioned in a patient's body and as energy is transmitted to the retainer from the energy transmission member 174. It is contemplated that the shield 220 could be constructed in such a manner as to extend completely around the retainer 30. This would allow use of the applicator assembly 172 in a moist environment or in an aqueous environment in which the retainer is completely or almost completely submerged in liquid.

The force transmitting member 176 has a flange 204 which engages the groove 142 in the same manner as which the member 140 is schematically depicted as engaging a groove 142 in FIG. 8. However, it is contemplated that the flange 204 could be eliminated and a circular end plate provided at the distal end of the force transmitting member 176. The use of a plate would provide for a wider area of engagement of the force transmitting member 176 with the lower section 46 of the retainer 30. The use of a circular end plate in place of the flange 204 would allow the groove 142 in the lower section 46 of the retainer to be eliminated.

Prior to connecting the retainer 30 with the suture 36, the portions 32 and 34 of the suture are pulled with a predetermined tension. Tensioning the suture with a predetermined force may be accomplished in the manner disclosed in the aforementioned U.S. patent application Ser. No. 09/556,458 filed May 3, 2000 by Peter M. Bonutti and entitled Method and Apparatus For Securing Tissue or in the manner disclosed in U.S. patent application Ser. No. 10/102,413 filed Mar. 20, 2002 by Peter M. Bonutti and entitled Methods of Securing Body Tissue. Once a desired tension has been established in the intermediate portion 38 (FIG. 1) of the suture 36, the applicator assembly 172 is utilized to interconnect the lower section 46 and upper section 48 of the retainer in the manner previously discussed.

Since the portions 32 and 34 of the suture 36 were positioned in the passages 52 and 54 on opposite sides of the center projection 72, the portion 32 of the suture applies force against the lower section 46 of the retainer on the right (as viewed in FIG. 7) side of the central axis of the retainer. The portion 34 of the suture applies force against the lower section 46 of the retainer on the left side of the center projection 72. This results in the application of offsetting movements to the lower section 46 of the retainer. Therefore, the retainer 30 does not tend to rotate on an axis disposed between the portions 32 and 34 of the suture 36 and is stable relative to the body tissue 40.

Although it is believed that it may be desired to use the applicator assembly 172 to position the retainer 30 relative to body tissue, it should be understood that other ways of positioning the retainer elative to body tissue may be utilized. For example, a surgeon may grasp the retainer 30 with one hand and tension the portions 32 and 34 of the suture 36 with the other hand. The surgeon would then manually apply force against the retainer 30 to slide the retainer along the tensioned portions 32 and 34 of the suture toward the body tissue. Rather than gripping the retainer 30 with one hand, the surgeon may grip the retainer 30 with a manually actuated instrument.

If the retainer 30 is manually positioned relative to body tissue or positioned with a manually actuated instrument, a source of energy will have to be provided to interconnect the sections 46 and 48 of the retainer. The energy source may have any of the constructions disclosed in U.S. Pat. No. 6,368,343. Alternatively, the energy source may have the construction disclosed in U.S. Pat. No. 3,513,848.

Looped Suture

Figure 13:
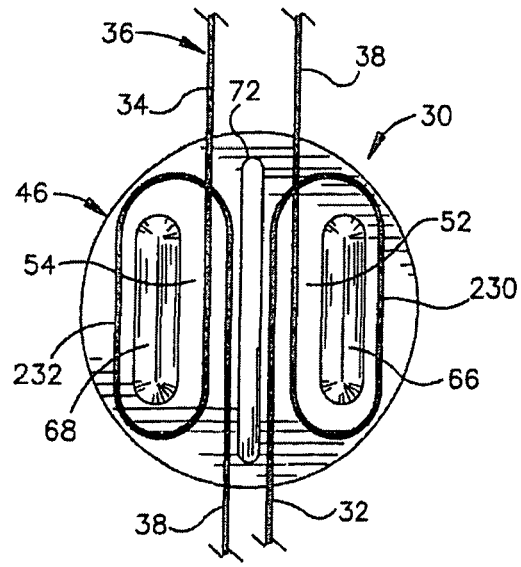
FIG. 13. is a schematic illustration depicting the manner in which a suture may be looped around projections on the retainer of FIGS. 1-8.

In FIGS. 1-8, the portions 34 and 36 of the suture extend straight through the retainer 30 in a generally parallel relationship with each other. However, it is contemplated that the portions 34 and 36 of the suture may be looped around portions of the retainer to increase the strength of the connection between the suture 36 and the retainer 30. In the embodiment of FIG. 13, the suture is looped around the projections 66 and 68 from the upper section 48 of the retainer. By looping the portions 32 and 34 of the suture around the projections 66 and 68, in the manner illustrated in FIG. 13, the strength of the grip which the retainer 30 obtains on the suture is increased.

When the suture 36 is to be positioned relative to the retainer 30 and looped around the projections 66 and 68, in the manner illustrated schematically in FIG. 13, the portion 32 of the suture is inserted through the passage 52 between the right projection 66 from the upper section 48 of the retainer. The portion 32 of the suture is then wrapped around the projection 66 and again inserted through the passage 52 to form a loop around the projection 66. The portion 34 of the suture 36 is looped around the projection 68 from the upper section 48 of the retainer 30 in the same manner as in which the portion 32 of the suture is looped around the projection 66.

As was previously mentioned, the portions 32 and 34 of the suture 36 are moved in opposite directions into the retainer 30. Thus, when the portion 32 of the suture 36 is initially moved through the passage 52, the suture is moved downward (as viewed in FIG. 13) through the passage and then wrapped upwardly around the projection 66 in a counter clockwise direction (as viewed in FIG. 13) and again moved downward through the passage 52. When the portion 34 of the suture is to be positioned in the passage 54 in the retainer 30, the portion 34 of the suture is first moved upward (as viewed in FIG. 13) through the passage 54 and then wrapped in a counter clockwise direction about the projection 68. As the portion 34 of the suture is wrapped around the projection 68, the portion 34 of the suture is again inserted through the passage 54. This results in the formation of a loop 232 around the projection 68. The intermediate portion 38 of the suture 36 extends upward (as viewed in FIG. 13) from the loop 230 and extends downward (as viewed in FIG. 13) from the loop 232.

Once the loops 230 and 232 have been formed in the portions 32 and 34 of the suture 36, the retainer 30 is gripped by the applicator assembly 172 and moved along the suture 36 toward the body tissue in the manner previously discussed. Movement of the retainer along the suture 36 toward the body tissue will, to some extent, be impeded by the loops 230 and 232 in the suture 36. By applying force with a handle 194 of the applicator assembly 172, the retainer 30 can be moved along the suture 36 toward the body tissue after the loops 230 and 232 have been formed in the suture 36. It should be understood that the retainer 30 may be manually moved along the suture 36 or moved along the suture with an applicator assembly having a construction which is different than the construction of the applicator assembly 172.

Although the loops 230 and 232 have been illustrated as being formed around the projections 66 and 68 from the upper section 48 of the retainer 30, it is contemplated that the loops could be formed around a different portion of the retainer 30 if desired. For example, one or both of the loops 230 and 232 could be formed around the center projection 72.

Alternatively, both of the loops 230 and 232 could be formed around both of the projections 66 and 68. When this is to be done, the portion 32 of the suture 36 would be moved downward (as viewed in FIG. 13) through the passage 52 and looped around the outside of the projection 66 across the upper (as viewed in FIG. 13) end portion of the center projection 72 and downward around the left projection 68, across the bottom (as viewed in FIG. 13) of the center projection 72 and again wrapped around the outside of the right projection 66. The portion 32 of the suture 36 would then be moved downward for a second time, through the passage 52. Similarly, the portion 34 of the suture 36 is moved upward (as viewed in FIG. 13) through the passage 54, downward around the left projection 68, across the lower (as viewed in FIG. 13) end of the center projection 72 upward around the outside of the right projection 66. The loop would then be moved across the upper end portion of the center projection 72 and downward (as viewed in FIG. 13) for a second time across the outside of the left projection 68. The portion 34 of the suture 36 would then again be moved upward through the passage 54.

Figure 14:
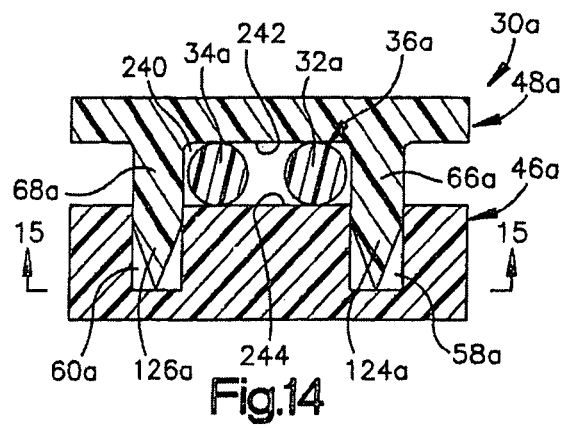
FIG. 14. is a schematic sectional view, generally similar to FIG. 7 illustrating a second embodiment of the retainer.
Figure 15:
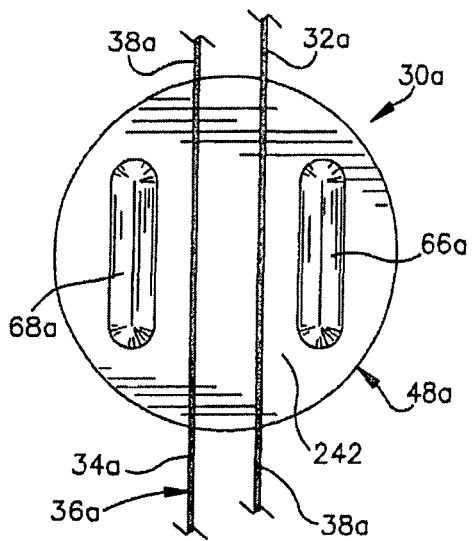
FIG. 15. is a schematic illustration, taken generally along the line of 15-15 of FIG. 14, illustrating a relationship of the suture to a cover section of the retainer.
Figure 16:
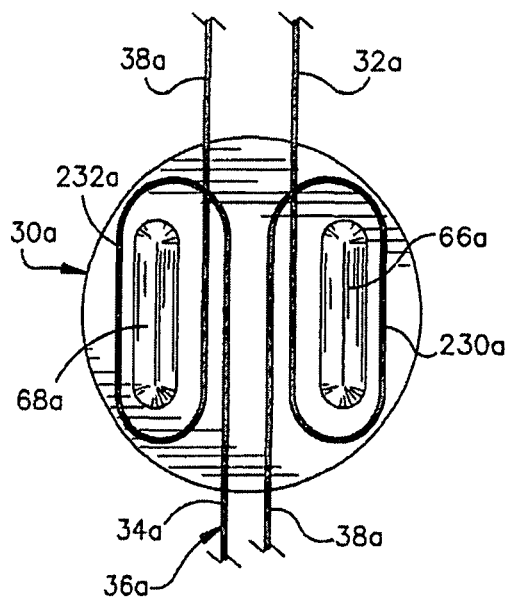
FIG. 16. is a schematic illustration, generally similar to FIG. 15, illustrating the manner in which the suture may be looped around projections on the cover section of the retainer.

Embodiment of FIGS. 14-16

In the embodiment of the retainer illustrated in FIGS. 1-8, the retainer 30 has a center projection 72 which cooperates with the right and left projections 66 and 68 to form the two elongated passages through which the portions 32 and 34 of the suture are moved in opposite directions. In the embodiment of the invention illustrated in FIGS. 14-16, the center projection on the retainer is omitted. Since the embodiment of the invention illustrated in FIGS. 14-16 is generally similar to the embodiment of the invention illustrated in FIGS. 1-8, similar numerals will be utilized to identify similar components, the suffix "a" being associated with the numerals of FIGS. 14-16 to avoid confusion.

A retainer 30a includes a lower section 46a and an upper section 48a. The lower section 46a has a pair of recesses 58a and 60a. The recesses 58a and 60a have the configuration as the recesses 58 and 60 of FIGS. 1-8. Right and left projections 66a and 68a extend downward (as viewed in FIG. 14) from the upper section 48a into the recesses 58a and 60a in the lower section 60a. There is an interference fit between the projections 66a and 68a and the recesses 58a and 60a to hold the upper section 48a in a desired spatial relationship with the lower section 46a of the retainer 30a. In the embodiment of the invention illustrated in FIG. 15, the portions 32a and 34a of the suture 36a are disposed in a side-by-side relationship in a single passage 240 (FIG. 14) which extends between projections 66a and 68a from the portion 48a of the retainer 30a.

When the retainer 30a is gripped by the applicator assembly 172 with a constant predetermined force, end portions 124a and 126a (FIG. 14) of the projections 66a and 68a are pressed against bottom surfaces of the recesses 58a and 60a in the manner previously described in conjunction with the embodiment of the invention illustrated in FIGS. 1-8. The projections 66a and 68a have the same configuration as the projections 66 and 68 of FIGS. 3-7. Therefore, there is line contact between the tapered end portions 124a and 126a of the projections 66a and 68a and the flat bottom surfaces of the recesses 58a and 60a.

The portions 32a and 34a of the suture 36a are inserted in opposite directions through the passage 240 formed between the lower section 46a and upper section 48a of the retainer 30a. The retainer 30a is slid along the suture 36a to a desired position relative to body tissue while the retainer is gripped with a constant predetermined force by the applicator assembly 172. If desired, the retainer 30a may be manually gripped and slid along the portions 32a and 34a of the suture 36a.

If the retainer 30a is manually positioned relative to body tissue, a suitable source of energy will have to be provided to effect heating of the retainer. This source of energy may have any one of the constructions disclosed in U.S. Pat. Nos. 3,513, 848 and 6,368,343. Alternatively, the source of energy may have a known construction and be a source of thermal in light (laser) energy.

Assuming that the applicator assembly 172 is utilized to position the retainer 30, when the foot pedal actuated switch 214 (FIG. 9) is closed, ultrasonic vibratory energy is transmitted from the source 212 through the energy transmission member 174 to the retainer 30a (FIG. 14). The tapered end portions 124a and 126a of the projections 66a and 68a function as energy directors and concentrate the ultrasonic vibratory energy from the source 212. As this occurs, the end portions 124a and 126a of the projections 66a and 68a are softened and deformed under the influence of the constant predetermined force applied against the retainer 30a by the applicator assembly 172 As this occurs, the distance between the lower section 46a and upper section 48a is decreased and the portions 32a and 34a of the suture 36a are gripped between flat gripper surfaces 242 and 244 formed on the upper section 48a and lower section 46a of the retainer 30a.

In FIG. 15, the portions 32a and 34a of the suture 36a extend straight through the passage in opposite directions. In the embodiment illustrated in FIG. 16, the portions 32a and 34a of the suture are looped around the projections 66a and 68a in the same manner as previously described in conjunction with FIG. 13. This results in the formation of loops 230a and 232a around the projections 66a and 68a. By wrapping the portions 32a and 34a of the suture 36a around the projections 66a and 68a, the portions 32a and 34a are positioned in the passage 240 at locations equal distances from the center of the retainer 30a. This minimizes any movement resulting from forces applied to the retainer 30a by the suture 36a and increases the stability of the retainer on the body tissue.

In the embodiment of the invention illustrated in FIGS. 1-8 and 14-16, the lower section 46 is provided with recesses 58 and 60. However, it is contemplated that the recesses 58 and 60 may be omitted if desired. If the recesses 58 and 60 are omitted, the projections 66 and 68 (FIGS. 7 and 8) will engage a flat upper side surface on the base section 46. With this construction, the pointed end portions 124a and 126a (FIG. 14) of the projections 66a and 68a will engage a flat surface 244 on the base section 46a.

When the recesses 58 and 60 are omitted, it may be desired to provide other structure to maintain the lower and upper sections 46 and 48 of the retainer in a desired spatial relationship during insertion of the suture 36 into a passage 24 or passages 52 and 54. For example, the center projection 72 (FIG. 3) may extend into an opening through the upper section 48. An interference fit may be provided between the center projection and the opening in the upper section 48. Alternatively, a guide surface connected with the lower section 46 of the retainer may engage a guide surface on the upper section 48.

Figure 17:
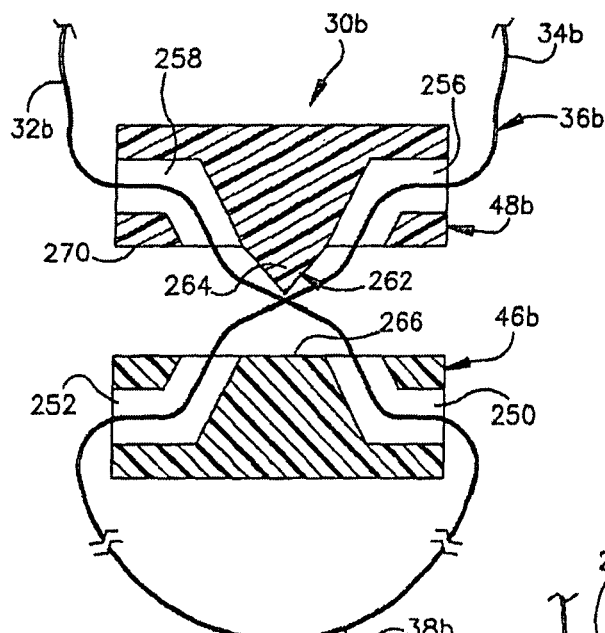
FIG. 17. is a schematic sectional view of another embodiment of the retainer.

Embodiment of FIG. 17

In the embodiments of the invention illustrated in FIGS. 1-8 and 14-16, a plurality of projections from the upper section 48 engage recesses in the lower section 46. In the embodiment of the illustrated in FIG. 17, a single projection from the upper section engages an upper side of the lower section. Since the embodiment of the invention illustrated in FIG. 17 is generally similar to the embodiments of the invention illustrated in FIGS. 1-8 and 14-16, similar numerals will be utilized to identify similar components, the suffix letter "b" being added to the numerals of FIG. 17 to avoid confusion.

A retainer 30b includes a lower or base section 46b and an upper or cover section 48b. A right passage 250 and a left passage 252 are formed in the lower section 46b. Similarly, a right passage 256 and a left passage 258 are formed in the upper section 48b. A suture 36b extends through the passages 250, 252, 256 and 258 in the lower and upper sections 46b and 48b of the retainer 30b. The suture 36b includes end portions 32b and 34b which are interconnected by an intermediate portion 38b. The intermediate portion 38b of the suture 36b extends around body tissue in much the same manner as is illustrated schematically in FIG. 1 for the suture 36.

A single projection 262 extends from the upper section 48b of the retainer 30b. The projection 262 is offset to one side of the suture 36b. The projection 262 has a pointed end portion 264 which is engagable with a flat upper side surface 266 on the lower portion 46b of the retainer 30b. The pointed end portion 264 of the projection 262 has the same general configuration as the pointed end portions 124 and 126 of the projections 66 and 68 in FIG. 7. However, the pointed end portion 264 of the projection 262 may have a conical configuration if desired.

If desired, a pair of projections, corresponding to the projections 66 and 68, may be provided. If this is done, one of the projections would be offset from the suture 36b in a direction into the page on which FIG. 17 is disposed and the other projection would be offset from the suture 36b in a direction out of the page on which FIG. 17 is disposed. This would result in a passage being formed between the two projections so that the portions 32b and 34b of the suture 36b would both extend through a passage between the projections.

When the suture 36b and retainer 30b are to be connected with body tissue, the suture may be positioned relative to the body tissue in the manner previously described in conjunction with in the embodiment of the invention illustrated in FIGS. 1-8. As was previously mentioned, this may be done using minimally invasive surgical techniques. The suture 36b may be moved into a patient's body through a cannula and positioned relative to tissue in the patient's body. The end portions 32b and 34b of the suture may extend through the cannula and be accessible to a surgeon.

The portion 32b of the suture 36b is inserted through the nonlinear passage 250 in the lower section 46b and through the nonlinear passage 258 in the upper section 48b of the retainer 30b. The portion 34b of the suture is inserted through the nonlinear passage 252 in the lower portion 46b and through the nonlinear passage 256 in the upper portion 48b, in the manner indicated schematically in FIG. 17. The lower section 46b and upper section 48b are then gripped by an applicator assembly which may have the same construction as the applicator assembly 172 of FIGS. 9-12.

While the retainer 30b is gripped with a constant predetermined force by the applicator assembly 172, the surgeon grips the applicator assembly with one hand and the portions 32b and 34b of the suture 36b with the other hand. The retainer 30b is then slid along the suture 36b toward the body tissue around which the intermediate portion 38b of the suture extends. As this occurs, the end portion (FIG. 12) of the applicator assembly 172 moves through the cannula and slides the retainer 30b along the suture 36b to a position that is engagement with the body tissue, that is, to a position similar to that in FIG. 1 for the retainer 30. While the retainer 30b is being slid along the suture 36b, the applicator assembly grips the retainer with a constant predetermined force.

If desired, the retainer 30b may be positioned relative to the suture 36b and body tissue in a way other than use of the applicator assembly 172. For example, the retainer 30b may be gripped by one hand of a surgeon and the portions 32b and 34b of the suture gripped and tensioned with the other hand. The manual application of force to the retainer 30b would slide the retainer along the suture 36b.

Once the retainer 30b has been positioned relative to the body tissue and the suture 36b is tensioned with a desired force, energy is conducted from a source of energy, similar to the energy source 212 of FIG. 9, to the energy transmission member 174 and the retainer 30b. It is contemplated that many different types of energy could be transmitted to the retainer 30b. For example, radio frequency, ultrasonic, heat, or light energy may be transmitted to the retainer 30b through an energy transmission member. In the embodiment of the applicator assembly 172 illustrated in FIGS. 9-12, ultrasonic vibratory energy is conducted to the retainer 30b through energy transmission member 174 while the applicator assembly 172 grips the retainer 30b with a constant predetermined force.

The projection 262 functions as an energy director which concentrates energy applied to the upper section 48 of the retainer 30b by the end surface 206 of the energy transmission member 174 (FIG. 9). The concentrated ultrasonic vibratory energy transmitted from the energy transmission member 174 heats the material of the projection 262 (FIG. 17) and the material of the base section 46b engaged by the projection into its transition temperature range. As this occurs, there is a softening and deforming of the material of the projection 262.

A flat lower side surface 270 on the upper portion 48b of the retainer 30b and the flat upper side surface 266 of the lower portion 46b of the retainer move into engagement with each other. Material of the retainer 30b tends to flow into the passages 250, 252, 256 and 258 formed in the lower and upper sections 46b and 48b of the retainer 30b. The portions 32b and 34b of the suture 36b are firmly clamped between the side surfaces 266 and 270 on the lower section 46b and upper section 48b of the retainer 30b.

As the material of the retainer 30b cools and the applicator assembly 172 is disengaged from the retainer, there may be a limited amount of bonding of the material of the retainer 30b to the portions 32b and 34b of the suture 36b. Although the suture 36b is, to some extent, deformed by force transmitted between the side surfaces 266 and 270 on the lower section 46b and upper section 48 of the retainer 30b, in the manner illustrated schematically in FIG. 8 for the suture 36, the deformation of the suture does not weaken the suture.

It is contemplated that the sections 46b and 48b of the retainer 30b may be made of many different polymeric materials. The sections 46b and 48b of the retainer 30b may be formed of polymers or copolymers. It is contemplated that the retainer 30b may be formed of biodegradable or nonbiodegradable materials. In one specific instance, the retainer was made from Poly-L-lactic acid (PLLA) which is a resorbable polymer.

The suture 36b may be formed by a single filament or a plurality of filaments. The suture 36b may be formed of biodegradable or nonbiodegradable material. It is contemplated that it may be desired to form the suture 36b of the same material as the retainer 30b. However, the retainer 30b and suture 36b may be formed of different materials.

Although the foregoing description in the manner in which the retainer 30b and 36b are positioned relative to body tissue have been in conjunction with manual positioning of the applicator assembly 172 by a surgeon, it is contemplated that a robotic mechanism may be utilized to position the retainer 30b and/or suture 36b relative to body tissue. Thus, a robotic mechanism may be utilize in association with the retainer 30b and/or suture 36b in the manner described in the aforementioned U.S. patent application Ser. No. 10/102,413 filed Mar. 20, 2002 by Peter M. Bonutti and entitled Methods of Securing Body Tissue. It is contemplated that imaging apparatus may be utilized in association with the positioning of the retainer 30b and/or suture 36b in the manner disclosed in the aforementioned U.S. patent application Ser. No. 10/102,413 filed Mar. 20, 2002 by Peter M. Bonutti.

Figure 18:
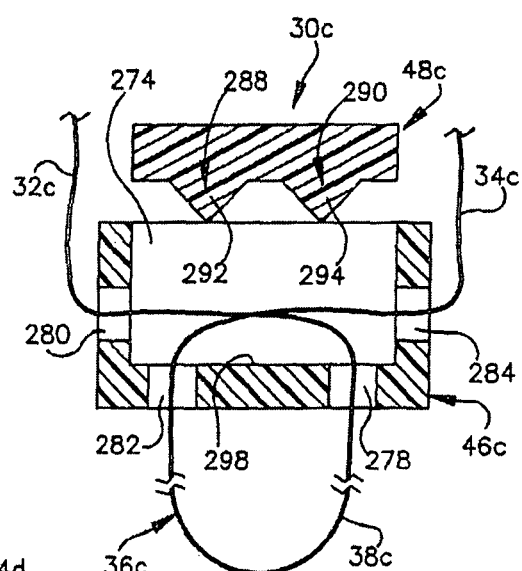
FIG. 18. is a schematic sectional view of another embodiment of the retainer.

Embodiment of FIG. 18

In the embodiment of the invention illustrated in FIG. 18, one of the sections of the retainer has a recess which receives the other section of the retainer. Since the embodiment of the invention illustrated in FIG. 18 is generally similar to the embodiments of the invention illustrated in FIGS. 1-8, and 14-17, similar numerals will be utilized to designate similar components, the suffix letter "c" being associated with the numerals of FIG. 18 to avoid confusion.

A retainer 30c (FIG. 18) includes a lower or base section 46c and an upper or cover section 48c. A suture 36c has portions 32c and 34c which extend through the retainer 30c. An intermediate portion 38c of the suture may extend around body tissue in the manner disclosed in FIG. 1. Of course, the suture 36c may be connected with either hard or soft body tissue in any desired manner.

The lower section 46c of the retainer 30c has a cylindrical recess 274 which is sized so as to receive the circular upper section 48c of the retainer 30c. The lower section 46c of the retainer has passages 278 and 280 through which the portion 32c of the suture 36c extends. In addition, the lower section 46c of the retainer 30c has passages 282 and 284 through which the portion 34c of the suture 36c extends. The recess 274 cooperates with the passages 278, 280, 282 and 284 to form a central passage through which both portions 32c and 34c of the suture extend.

A pair of projections 288 and 290 extend from the upper section 48c of the retainer 30c toward the lower section 46c of the retainer. The projections 288 and 290 have pointed end portions 292 and 294 which function as energy directors and concentrate ultrasonic vibratory energy transmitted from the applicator assembly 172 (FIG. 9) to the upper section 48c of the retainer 30c. The projections 288 and 290 are offset from the portions of the suture 36c. One of the projections, for example, the projection 288, may be offset in a direction into the page on which FIG. 18 is disposed and the other projection, that is the projection 290, may be offset in a direction out of the page on which FIG. 18 is disposed.

When the suture 36c and retainer 30c are to be utilized in association with body tissue, the suture 36c is positioned relative to the body tissue. The portion 32c of the suture 36c is then moved through the passages 278 and 280 in the lower section 46c of the retainer 30c. The portion 34c of the suture 36c is moved through the passages 282 and 284 of the lower section 46c of the retainer 30c.

The upper section 48c of the retainer 30c is then positioned in the recess 274 with the projections 288 and 290 disposed in linear engagement with a flat upwardly facing side surface 298 on the lower section 46c of the retainer 30c. The pointed ends of the projections 292 and 294 do not engage the suture 36c The retainer 30c is gripped by the distal end portion (FIG. 12) of the applicator assembly 172. This results in the retainer 30c being gripped with a constant predetermined force transmitted to the retainer 30c from the biasing spring 180 (FIG. 9) through the force transmitting member 176.

While the surgeon grips the handle 194 of the applicator assembly 172 with one hand and grips the portions 32c and 34c of the suture 36c with the other hand, the retainer 30c and leading end portion of the applicator assembly 172 are moved toward the body tissue. As this occurs, the retainer 30c is slid along the portions 32c and 34c of the suture 36c. While the retainer 30c is slid along the suture 36c, the retainer is gripped with a constant predetermined force by the applicator assembly 172.

When the retainer 30c is positioned in a desired location relative to the suture 36c and body tissue, energy is transmitted from the applicator assembly 172 to the retainer 30c to interconnect the lower section 46c and upper section 48c of the retainer 30c. During the transmission of energy to the retainer 30c to interconnect the lower section 46c and upper section 48c of the retainer, the applicator assembly 172 applies a constant predetermined clamping or gripping force to the retainer 30c. Ultrasonic vibratory energy is transmitted from the end surface 206 on the energy transmission member 174 to the upper section 48c of the retainer 30c. The pointed end portions 292 and 294 of the projections 288 and 290 engage the flat side surface 298 on the lower section 46c of the retainer. The pointed end portions 292 and 294 of the projection 288 act as energy directors which concentrate energy at the pointed end portions of the projections and at the portion of the surface 298 and engaged by the projections.

This energy heats the projections 288 and 290 and portions of the lower section 46c into a transition temperature range. As this occurs, the material of the projections 288 and 290 softens and flows relative to the suture 36c and lower and upper sections 46c and 48c of the retainer 30c. The lower and upper sections 46c and 48c of the retainer 30c are clamped together with a constant predetermined force by the applicator assembly 172 as the material of the projections 288 and 290 is heated. The lower and upper sections 46c and 48c of the retainer 30c grip the suture 36c with a clamping action.

Material of the retainer 36c is subsequently allowed to cool and the trigger 198 on the applicator assembly 172 is actuated to release retainer 30c. As the material of the retainer 30c cools, the lower section 46c and upper section 48c of the retainer are bonded together. In addition, there is some bonding of the material of the retainer 30c to the suture 36c. However, the suture 36c is primarily secured against movement relative the retainer 30c by clamping the portions 32c and 34c of the suture 36c between the lower section 46c and the upper section 48c of the retainer 30c. Although the suture 36c is slightly deformed, in the manner illustrated schematically in FIG. 8, there is no significant weakening of the suture 36c.

It is contemplated that the suture 36c and retainer 30c may be positioned relative to body tissue during minimally invasive surgery. The suture 36c and retainer 30c may be positioned relative to the body tissue by being moved through a cannula. If desired, a robotic mechanism may be utilized to position the suture 36c and/or retainer 30c relative to the body tissue.

In the embodiment of the invention illustrated in FIG. 18, the upper section 48c of the retainer 30c is separate from the lower section 46c and is manually moved into the recess 274 after the portions 32c and 34c of the suture 36c have been positioned in the passages 278, 280, 282 and 284. If desired, the upper section 48c of the retainer 30c could be connected with the lower section 46c. For example, the upper section 48c may be positioned in the recess 274. An interference fit may be provided between the lower and upper sections 46c and 48c to hold the upper section in the recess 274. Alternatively, one or more flexible connectors may be used to interconnect the lower and upper sections. The connector may be a flexible strap. If desired, the connector may be weak sections which are easily broken as the upper section 48c moves into the recess 274.

Figure 19:
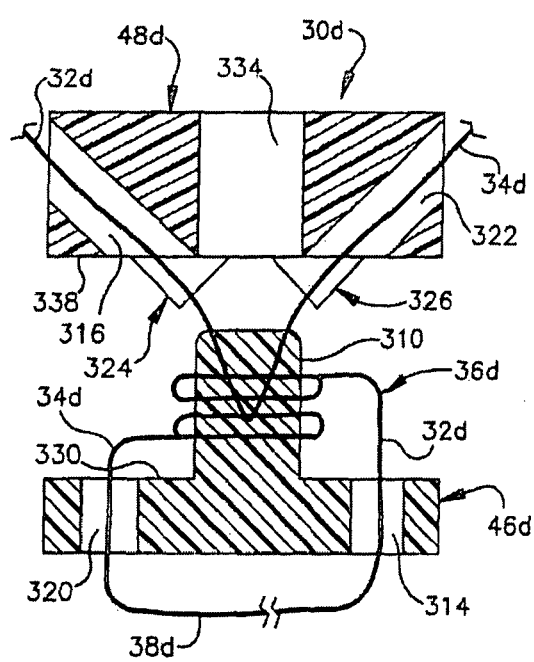
FIG. 19. is a schematic sectional view of another embodiment of the retainer.

Embodiment of FIG. 19

In the embodiments of the invention illustrated in FIGS. 1-8 and 14-18, the suture 36 extends through passages in the retainer 30 and is clamped in place. In the embodiment of the invention illustrated in FIG. 19, the suture extends through passages in the retainer and is wrapped around a portion of the retainer, in a manner similar to that previously described in conjunction with the embodiment of the invention illustrated in FIG. 13, prior to being clamped in place by interconnecting of the lower and upper sections of the retainer. Since the embodiment of the invention illustrated in FIG. 19 is generally similar to the embodiments of the invention illustrated in FIGS. 1-8 and 14-18, similar numerals will be utilized to indicate similar components, the suffix letter "d" being associated with the numerals of FIG. 19 to avoid confusion.

A retainer 30d is associated with a suture 36d. The retainer 30d has a lower section 46d and an upper section 48d. The suture 36d has a portion 32d and a portion 34d which extend through the retainer 30d. An intermediate portion 38d of the suture 36d extends between the portions 32d and 34d of the suture and may extend around body tissue in the manner illustrated schematically for the suture 36 in FIG. 1.

The lower section 46d of the retainer 30d has a cylindrical central projection or post 310. The portion 32d of the suture 36d extends through a passage 314 in the lower section 46d of the retainer 30d and is looped for a plurality of turns around the central projection 310. The portion 32d of the suture 36d extends from the loops around the central projection 310 through a passage 316 in the upper section 48d of the retainer 30d. Similarly, the portion 34d of the suture 36d extends through a passage 320 in the lower section 46d and is wrapped for a plurality of loops around the central projection 310. The portion 34d of the suture 36d extends from the central projection 310 through a passage 322 in the upper section 48d of the retainer 30d.

Projections 324 and 326 extend downward (as viewed in FIG. 19) from the upper section 48d toward a flat upper side surface 330 on the lower section 46d. The projections 324 and 326 are offset from the central projection 310 and from the openings 314 and 320 in the lower section 46d. Although only two projections 324 and 326 are illustrated in FIG. 19, a greater number of projections may be provided if desired.

The suture 36d is positioned relative to body tissue in the same manner as is illustrated schematically for the suture 36 in FIG. 1. This may be done during arthroscopic or laproscopic surgery. To minimize the size of an incision in a patient's body, the suture may be moved through a cannula into the patient's body and positioned relative to hard and/or soft body tissue. The portions 32d and 34d of the suture may extend from the cannula and be readily accessible to a surgeon.

The portion 32d of the suture is inserted through the passage 314 and wrapped for a plurality of turns around the central projection 310. The portion 34d of the suture is inserted through the passage 320 and is also wrapped for a plurality of turns around the central projection 310. The portion 34d of the suture is inserted through the passage 322 in the upper section 48d of the retainer 30d. The portion 32d of the suture 36d is inserted through the passage 316 in the upper section 48d of the retainer 30d.

The upper section 48d of the retainer 30d is moved along the portions 32d and 34d of the suture until the projections 324 and 326 from the upper section 48d of the retainer 30d engage the flat upper side surface 330 of the lower section 46d of the retainer. As this occurs, the central projection 310 enters a cylindrical opening 334 in the upper section 48d of the retainer 30d. As the central projection 310 is telescopically inserted into the opening 334, the turns of the portions 32d and 34d of the suture 36d are disposed around the central projection move downward (as viewed in FIG. 19) toward the flat surface 330 on the lower section 46d of the retainer 30d.

The projections 324 and 326 are offset from the portions 32d and 34d of the suture 36d. The pointed projections 324 and 326 engage the flat surface 330 on the lower section 46d of the retainer 30d. The projections 324 and 326 are spaced from the suture 36d and prevent the suture from being gripped between the lower section 46d and upper section 48d of the retainer 30d.

The retainer 30d is then gripped by the distal end portion of the applicator assembly 172 (FIG. 12). The applicator assembly 172 grips the retainer 30d with a constant force which is determined by the spring 180 (FIG. 9).

While the retainer 30d is gripped by the applicator assembly 172, the retainer is slid along the portions 32d and 34d (FIG. 19) of the suture 36d toward the body tissue. As this occurs, the distal end portion of the applicator assembly 172 and the retainer 30*d* may be moved through a cannula or through an open incision. Regardless of whether or not the retainer 30*d* is moved through a cannula, the retainer is positioned in engagement with body tissue, similar to the body tissue of 40 of FIG. 1, while the retainer is gripped with the predetermined constant force by the applicator assembly 172.

Once the retainer 30*d* has been positioned relative to the body tissue, the portions 32*d* and 34*d* of the suture 36*d* are tensioned with a predetermined force. While the suture 36*d* is tensioned with a predetermined force, ultrasonic vibratory energy is transmitted from a source of energy, corresponding to the energy source 212 of FIG. 9, to the retainer 30*d*. The energy is transmitted to the retainer 30*d* through the energy transmission member 174. The energy transmitted to the retainer 30*d* heats the projections 324 and 326 and the material of the lower section 46*d* of the retainer engaged by the projections.

The projections 324 and 326 have a pointed configuration and function as energy directors which concentrate the energy transmitted from the source 212. This results in heating of the projections 324 and 326 and a portion of the lower section 46*d* of the retainer 30*d* engaged by the projections to temperatures in the transition temperature range of the material of the retainer 30*d*. As this occurs, the lower and upper sections 46*d* and 48*d* of the retainer 30*d* are moved together under the influence of the constant predetermined force applied against the retainer by the applicator assembly 172. This results in the loops of the suture disposed around the central projection 310 being firmly gripped between the flat upper side surface 330 of the lower section 46*d* of the retainer and a flat lower side surface 338 on the upper section 48*d* of the retainer.

The trigger 198 on the applicator assembly 172 is then manually actuated to release the retainer 30*d*. As this occurs, the retainer 30*d* cools. A secure bond is formed between the lower section 46*d* and upper section 48*d* of the retainer at the locations where the projections 324 and 326 from the upper section 48*d* of the retainer engage the lower section 46*d* of the retainer. A robotic mechanism may be utilized to position the suture 36*d* and/or retainer 30*d* relative to body tissue.

It is contemplated that the retainer 30*d* and suture 36*d* may be formed of either biodegradable or nonbiodegradable material. The retainer 30*d* and suture 36*d* may be formed of the same materials or of different materials. For example, the suture 36*d* could be formed of a biodegradable material while the retainer 30*d* is formed of a nonbiodegradable material. Alternatively, both the suture 36*d* and retainer 30*d* may be formed of a biodegradable material.

Embodiment of FIGS. 20 and 21

In the embodiment of the invention illustrated in FIGS. 20 and 21, a suture is clamped between and held by sections of a retainer. Since the embodiment of the invention illustrated in FIGS. 20 and 21 is generally similar to the embodiments of the invention illustrated in FIGS. 1-8 and 13-19, similar numerals will be utilized to designate similar components, the suffix letter "e" being associated with the numerals of FIGS. 20 and 21 to avoid confusion.

A retainer 30*e* includes lower and upper sections 46*e* and 48*e*. A suture 36*e* (FIG. 20) has portions 32*e* and 34*e* which extend through the retainer 30*e*. The portions 32*e* and 34*e* of the suture 36*e* are interconnected by an intermediate portion 38*e* of the suture. A loop 230*e* is formed in the portion 32*e* of the suture 36*e* and extends around part of the lower section 46*e* of the retainer 30*e*. Similarly, a loop 232*e* is formed in the portion 34*e* of the suture 36*e* and extends around part of the lower section 46*e* of the retainer 30*e*.

The lower section 46*e* of the retainer 30*e* includes a circular bottom wall 344 (FIG. 21) having a flat upwardly facing side surface 346. A cylindrical side wall 350 extends upward from the bottom wall 344. The side wall 350 cooperates with the bottom wall 344 to form a cylindrical recess 274*e* (FIG. 21). The upper section 48*e* has a circular body 64*e* which has a diameter which is only slightly greater than an inside diameter cylindrical side wall 350*e*. This results in an interference fit between the upper section 48*e* and lower section 46*e* of the retainer 30*e* when the upper section 64*e* is inserted into the cylindrical recess 274*e*.

While the upper section 48*e* is held in the cylindrical recess 274*e* in the lower section 46*e* of the retainer 30*e*, the portions 32*e* and 34*e* of the suture 36*e* are inserted through the retainer 30*e* in opposite directions. Thus, the suture 32*e* is inserted through a passage 354 (FIG. 20) in the side wall 350 of the lower section 46*e* of the retainer 30*e*. The portion 32*e* of the suture is inserted through the recess 274*e* (FIG. 21) to a second passage 356 formed in the side wall 350 of the lower section 46*e* of the retainer.

The suture is wrapped around the outside of the side wall 350 and inserted through the passage 354 for a second time. The end portion 32*e* of the suture 36*e* is then moved through the passage 356*e* in the side wall for a second time. This forms the loop 230*e* around a portion of the side wall 350 in the manner illustrated schematically in FIG. 20.

Similarly, the portion 34*e* of the suture 36*e* is inserted through a passage 360 formed in the side wall 350 (FIGS. 20 and 21) into the cylindrical recess 274*e*. The portion 34*e* of the suture is inserted through the cylindrical recess 274*e* and through another passage 362 formed in the side wall 350 of the lower section 46*e* of the retainer 30*e*. The portion 34*e* of the suture 36*e* is wrapped around the outside of the side wall 350 (FIG. 20) and inserted for a second time through the passage 360. The portion 34*e* of the suture is inserted through the recess 274*e* and the opening 362*e* to form the loop 232*e* around the portion of the lower section 46*e* of the retainer 30*e*.

The upper section 48*e* of the retainer 30*e* has a plurality of pointed projections 366 and 368 (FIG. 20). When the upper section 48*e* of the retainer 30*e* is disposed in the recess 274*e*, the projections 366 and 368 are enclosed by the loops 230*e* and 232*e*. The projections 366 and 368 have pointed end portions with a configuration similar to the configuration of the pointed end portions 124 and 126 on the projections 66 and 68 of FIGS. 3-7. The end portions of the projections 366 and 368 engage the side surface 346 on the bottom wall 344 when the upper section 48*e* is disposed in the cylindrical recess 274*e*. There is line contact between the end portions of the projections 366 and 368 and the surface 346 on the bottom wall 344. The pointed end portions of the projections 366 and 368 are spaced from the suture 36*e*.

The upper section 48*e* of the retainer 30*e* has a second plurality of projections 374 and 376 (FIGS. 20 and 21). The projections 374 and 376 have the same configurations as the projections 366 and 368. The projections 374 and 376 have pointed end portions 378 and 380 (FIG. 21). The pointed end portions 378 and 380 on the projections 374 and 376 engage the flat side surface 346 on the bottom wall 344 when the upper section 48*e* of the retainer 30*e* is disposed in the cylindrical recess 274*e*. The projections 374 and 376 are disposed within the loop 332*e* formed in the portion 34*e* of the suture 36*e*. The pointed end portions of the projections 374 and 376 are spaced from the suture 36*e*.

When the retainer 30*e* and suture 36*e* are to be used to secure body tissue during a surgical procedure, the intermediate portion 38*e* of the suture is positioned relative to the body tissue. At this time, the upper section 48*e* of the retainer 30*e* is disposed in the cylindrical recess 274*e* in the lower section 46*e* and the projections 366, 368, 374 and 376 are disposed in engagement with the side surface 246 of the bottom wall 344 of the retainer. The upper section 48e of the retainer 30e is held in the recess 274e by an interference fit between a cylindrical inner side surface of the side wall 350 and an outer side surface of the body 64e of the upper section.

After the intermediate portion 38e of the suture 36e has been positioned relative to body tissue, the portion 32e of the suture is moved downward (as viewed in FIG. 20) through the passage 354 and along the projections 366 and 368. The portion 32e of the suture 36e is then moved through the passage 356 and wrapped around the outside of the retainer 30e. The portion 32e of the suture is again moved downward (as viewed in FIG. 20) through the passages 354 and 356 to form the loop 230e.

The portion 34e of the suture 36e is inserted upward (as viewed in FIG. 20) through the passage 360 and along the projections 374 and 376. The portion 34e of the suture is then moved through the passage 362 and wrapped around the outside of the bottom section 46e of the retainer 30e. The portion 34e of the suture is again upward (as viewed in FIG. 20) through the passages 360 and 362 to form the loop 232e. When this has been done, the portions 32e and 34e of the suture extend in opposite directions from the retainer 30e and the intermediate portion 38e of the suture extends in opposite directions from the retainer.

The retainer is then gripped with the distal end portion (FIG. 12) of the applicator assembly 172. The applicator assembly 172 grips the retainer 30e with a constant predetermined force.

While the retainer 30e is gripped with a constant predetermined force by the applicator assembly 172, a surgeon manually holds the handle 194 of the applicator assembly 172 (FIGS. 9 and 10) with one hand and tensions the portions 32e and 34e of the suture 36e with the other hand. While tensioning the suture 36e, the surgeon slides the retainer 30e along the suture toward the body tissue. As it was previously mentioned, this may involve moving of the retainer 30e and the distal end portion of the applicator assembly 172 through a cannula to position the retainer relative to the body tissue. A robotic mechanism may be utilized to position the suture 36e and/or retainer 30e relative to body tissue.

When the retainer has been positioned at a desired location relative to the body tissue in the manner similar to the schematic illustration of FIG. 1, energy is transmitted from the energy source 212 through the energy transmission member 174 to the retainer 30e. Although the energy is ultrasonic vibratory energy, it is contemplated that it could be a different type of energy if desired. For example, radio frequency, light, or thermal energy could be transmitted to the retainer 30e.

The ultrasonic vibratory energy transmitted to the retainer 30e is concentrated by the projections 366, 368, 374 and 376 which function as energy directors. The concentrated energy heats the projections 366, 368, 374 and 376 and the portion of the bottom wall 344 of the lower section 46e of the retainer 30e engaged by the projections, to a temperature in a transition temperature range for the material of the retainer. The retainer may be formed of a polymeric material which is a polymer or copolymer. The material of the retainer 30e may be biodegradable or nonbiodegradable.

As the projections 374 and 376 are heated and softened, the upper section 48e of the retainer is pressed toward the bottom wall 344 of the lower section 46e of the retainer 30e by the applicator assembly 172. The force applied against the retainer 30e is effective to cause the softened material of the projections 366, 368, 374 and 376 to flow in the recess 274e. As this occurs, the upper section 48e of the retainer 30e moves toward the bottom wall 344 of the lower section 46e of the retainer. This results in the portions 32e and 34e of the suture 36e being securely clamped between the lower section 46e and upper section 48e of the retainer 30e.

When the material of the projections 374 and 376 has cooled, the lower section 46e and upper section 48e of the retainer are securely bonded together to maintain a secure grip on the suture 36e. Although there may be some bonding of the material of the projections 366, 368, 374 and 376 to the suture 36e, there is no significant weakening of the suture.

Embodiment of FIG. 22

The retainer of the embodiment of the invention illustrated in FIG. 22 is generally similar to the retainers of FIGS. 1-8 and 13-21. Numerals similar to the numerals utilized in conjunction with FIGS. 1-8 and 13-21 will be utilized to designate similar components, the suffix letter "f" being associated with the numerals of FIG. 22 to avoid confusion.

A retainer 30f has a lower section 46f and an upper section 48f. A suture 36f has portions 32f and 34f which extend through the retainer 30f. An intermediate portion 38f of the suture 36f extends between the portions 32f and 34f and may extend around body tissue in the manner illustrated schematically in FIG. 1 for the suture 36.

The portion 32f of the suture 36f extends through a passage 384 in the lower section 46f of the retainer 30f. The portion 32f of the suture extends through a passage 386 formed in the upper section 48f of the retainer 30f. The portion 32f of the suture is wrapped around a portion 390 of the upper section 48f of the retainer 30f. The portion 32f of the suture is again inserted through the passage 386 to form a loop 230f around the portion 390 of the upper section 48f of the retainer 30f.

Similarly, the portion 34f of the suture 36f extends through a passage 394 in the lower section 46f of the retainer 30f. The portion 34f of the suture 36f extends through a passage 396 in the upper portion 48f of the retainer 30f. The portion 34f of the suture 36f is wrapped around a portion 398 of the upper section 48f of the retainer 30f to form a loop 232f.

Projection 400 extends from the upper section 48f of the retainer 30f. The projection 400 is engagable with a flat upper side surface 402 of the lower section 46f of the retainer 30f. The projection 400 has a pointed end portion which functions as an energy director which concentrates energy.

When the retainer 30f and suture 36f are utilized to secure body tissue, in a manner similar to that manner illustrated schematically in FIG. 1, the suture 36f is positioned relative to the body tissue with the intermediate portion 38f of the suture in engagement with the body tissue. The portion 32f of the suture is inserted through the passages 384 and 386 in the lower and upper sections 46f and 48f of the retainer 30f. The portion 32f of the suture is then wrapped around the portion 390 of the upper section 48f of the retainer 30f and again inserted through the passage 386.

The portion 34f of the suture 36f is inserted through the passage 394 in the lower section 46f of the retainer 30f and through the passage 396 in the upper section 48f of the retainer. The portion 34f of the suture 36f is wrapped around the portion 398 of the upper section 48f of the retainer 30f and again inserted through the passage 396.

The retainer 40f is then gripped by the distal end portion (FIG. 12) of the applicator assembly 172 (FIGS. 9 and 10). This results in the projection 400 being pressed against the upper side surface 402 of the lower section 46f of the retainer 30f with a predetermined constant force. While the retainer 30f is gripped by the distal end portion of the applicator assembly 172, a surgeon grips the portions 32f and 34f of the suture 36f with one hand and grips the handle 194 of the applicator assembly 172 with the other hand. While tensioning the portions 32f and 34f, the surgeon slides the retainer 30f along the suture 36f toward the body tissue. As it was previously mentioned, this may involve moving both the retainer 30f and the distal end portion of the applicator assembly 172 through a cannula.

A robotic mechanism may be utilized to position the suture 36f and/or retainer 30f relative to body tissue. Alternatively, the suture 36f and/or retainer 30f may be manually positioned relative to the body tissue.

Once the retainer 30f has been positioned relative to body tissue, energy is transmitted from a source 212 (FIG. 9) through the energy transmission member 174 to the retainer 30f. The pointed projection 400 functions as energy director and is effective to concentrate the ultrasonic vibratory energy in the projection 400 and in the portion of the lower section 48f of the retainer 30f engaged by the projection 400. The energy transmitted to the retainer 30f is effective to heat the projection 400 and the portion of the lower section 46f of the retainer engaged by the projection, into the transition temperature range for the material of the retainer 30f.

Once the material of the retainer 30f has been heat softened, the material can flow under the influence of the constant predetermined force with which the applicator assembly 172 grips the retainer 30f. This results in deformation of the projection 400 and movement of the lower and upper sections 46f and 48f of the retainer 30f together to clamp the portions 32f and 34f of the suture 36f between the flat upper side surface of the lower section 46f and flat lower side surface 404 of the upper section 48f of the retainer.

When the material of the retainer 30f has cooled, the trigger 198 on the applicator assembly 172 is actuated and the retainer is released. The lower and upper sections 46f and 48f of the retainer 30f are bonded together and maintain the clamping action against the portions 32f and 34f of the suture 36f to prevent relative movement between the retainer 30f and the suture 36.

Although only a single projection 400 has been illustrated schematically in FIG. 22, it should be understood that a plurality of projections may be provided. This would result in bonds being formed between the lower and upper section 46f and 48f of the retainer 30f at each of a plurality of projections.

Embodiment of FIG. 23

The embodiment of the invention illustrated in FIG. 23 is generally similar to the embodiments of FIGS. 1-8 and 13-22. Therefore, similar numerals will be utilized to designate similar components, the suffix letter "g" being associated with the numerals of FIG. 23 to avoid confusion.

A retainer 30g includes a lower section 46g and an upper section 48g. The retainer 30g may be formed of a polymeric material which is either a polymer or copolymer. The retainer 30g may be biodegradable or nonbiodegradable.

A suture 36g has a portion 32g which extends through the retainer 30g and a portion 34g which also extends through the retainer. The suture 36g may be formed of a plurality of filaments or a single filament. The suture 36g is formed of a polymeric material which is either a polymer or a copolymer. The suture 36g may be formed of a material which biodegradable or of a material which is nonbiodegradable. The retainer 30g and suture 36g may be formed of the same material or of different materials.

When the retainer 30g and suture 36g are to be used to secure body tissue, in a manner similar to the manner illustrated schematically in FIG. 1, an intermediate portion 38g of the suture is positioned around body tissue. The portions 32g and 34g of the suture 36g are then positioned relative to the lower and upper sections 46g and 48g of the retainer 30g.

When this is to be done, a portion 32g of the suture 36g is inserted through a passage 410 in the lower section 46g of the retainer 30g. The portion 32g of the suture 36g is wrapped around a portion 412 of the lower section 46g of the retainer 30g. The portion 32g of the suture is then inserted through the passage 410 for a second time forms a loop 230g around the portion 412 of the lower section 46g of the retainer 30g. The portion 32g of the suture 36g is then inserted through a passage 414 in the upper section 48g of the retainer 30g.

Similarly, the portion 34g of the suture 36g is inserted through a passage 420 in the lower section 46g of the retainer 30g. The portion 34g of the suture 36g is then wrapped around the portion 422 of the lower section 46g to form a loop 232g. The portion 34g of the suture 36g is then inserted through the passage 420 for a second time. The portion 34g of the suture 36g is then inserted through a passage 426 in the upper section 48g of the retainer 30g.

The sections 46g and 48g of the retainer 30g are then moved together. As this occurs, a projection 400g from the upper section 48g moves into engagement with a flat upper side surface 402g on the lower section 46g of the retainer 30g. The retainer 30g is then gripped with the distal end portion (FIG. 12) of the applicator assembly 172. The applicator assembly 172 grips the retainer 30g with a constant predetermined force.

When the retainer 30g and suture 36g are to be utilized to secure body tissue, in the manner similar to that illustrated schematically in FIG. 1, the suture 36g is positioned with the intermediate portion 38g of the suture extending around the body tissue. The portions 32g and 34g of the suture 36g are positioned relative to the upper and lower sections 46g and 48g in the manner previously described and illustrated schematically in FIG. 23.

While the surgeon grips the handle 194 of the applicator assembly 172 with one hand and grips the portions 32g and 34g of the suture 36g with the other hand, the retainer 30g is slid along the suture toward the body tissue. As the retainer 30g is slid along the suture 36g toward the body tissue, the retainer is gripped with a constant predetermined force by the applicator assembly 172. When the retainer 30g has been moved to a desired position relative to the body tissue, energy is transmitted from the source 212 to the energy transmission member 174. Although many different types of energy may be utilized, the energy transmitted to the retainer 30g from the energy transmission member 174 is ultrasonic vibratory energy.

The projection 40g has a pointed configuration and functions as an energy director which concentrates the ultrasonic vibratory energy transmitted from the energy transmission member 174 to the retainer 30g. The projection 400g and the material of the lower section 46g engaged by the projection are heated into their transition temperature ranges. Heating of the materials of the projection 400g into its transition temperature range enables the material to flow under the influence of the constant predetermined force applied against the retainer 30g by the applicator assembly 172. This results in the suture 36g being firmly clamped between the flat upper side surface 402g of the lower section 46g and a flat lower side surface 404g of the upper section 48g of the retainer 30g. The material of the projection 400g bonds to the material of the lower section 46g of the retainer 30g. This results in the clamping force applied against the suture 36g by the lower and upper sections 46g and 48g of the retainer 30g being maintained.

Although only a single projection 400g has been illustrated schematically in FIG. 23, it is contemplated that a plurality of projections may be provided. Each of the projections from the upper section 48g of the retainer 30g would engage the upper side surface 402g of the lower section 46g of the retainer. This would result in a plurality of bonds being formed between the lower section 46g and upper section 48g of the retainer.

Embodiment of FIG. 24

It is contemplated that the applicator assembly 172 (FIGS. 9-12) may be utilized to position any one of the retainers of FIGS. 1-8 and 13-23 relative to body tissue 40. The applicator assembly 172 is operable to bond upper and lower sections of any one of the retainers disclosed herein together to maintain a secure grip on portions 32 and 34 of the sutures 36. It should be understood that the applicator assembly 172 may be used with retainers other than the retainers disclosed herein.

In the embodiment of FIG. 24, the applicator assembly 172, retainer 30 and suture 36 have been illustrated in associated with a cannula 450. It should be understood that the applicator assembly 172, suture 36 and any one of the retainers 30 disclosed herein may be utilized without the cannula 450. However, by using the cannula 450, it is believed that minimally invasive surgery will be facilitated. Of course, the suture 36, retainer 30, and applicator assembly 172 may be utilized during surgical procedures which are not minimally invasive surgical procedures.

When the cannula 450 is to be utilized during a surgical procedure, the cannula is moved through body tissue 452 to a position in which a distal end portion 454 of the cannula 450 is adjacent to the body tissue 40 to be engaged by the suture 36. The proximal end portion 456 of the cannula 450 extends from the body tissue 452 in the manner illustrated schematically in FIG. 24. Once the cannula 450 has been positioned relative to the body tissue 40, the suture 36 is moved through the cannula and positioned relative to the body tissue. The portions 32 and/or 34 of the suture may be moved through the cannula 450 to position the suture relative to the body tissue. The portions 32 and/or 34 of the suture are then pulled from the cannula 450 with the intermediate portion 38 of the suture engaging the body tissue 40.

The portions 32 and 34 of the suture 36 are then inserted through one or more passages in the retainer 30. Once the portions 32 and 34 of the suture have been inserted through the retainer 30, the retainer is gripped by the applicator assembly 172 in the manner illustrated schematically in FIG. 24. When the retainer 30 is gripped by the applicator assembly 172, a constant predetermined force is applied against the retainer 30 by the applicator assembly 172.

A surgeon may then manually grasp the portions 32 and 34 of the suture and tension the suture. At the same time, the surgeon manually grasps the handle 194 (FIG. 10) on the applicator assembly 172 and moves the applicator assembly downward (as viewed in FIG. 24) toward the cannula 450. As this occurs, the retainer 30 slides along the portions 32 and 34 of the suture and approaches the proximal end portion 456 of the cannula 450.

Continued movement of the applicator assembly 172 toward the body tissue 40 slides the retainer 30 along the portions 32 and 34 of the suture 36 as the leading end portion of the applicator assembly and retainer enter the cannula. The downward (as viewed in FIG. 24) movement of the applicator assembly 172 and retainer 30 is continued while tension is maintained in the portions 32 and 34 of the suture 36. This results in the retainer 30 sliding along the portions 32 and 34 of the suture 36 as the retainer 30 is moved through the cannula 450 by the applicator assembly 172.

The retainer 30 and leading end portion of the applicator assembly 172 may be moved through the distal end portion 454 of the cannula 450 and positioned in engagement with the body tissue 40. Alternatively, the distal end portion 454 of the cannula may be placed in engagement with the body tissue and the retainer moved into engagement with a surface area of the body tissue 40 which is surrounded by the distal end portion 454 of the cannula 450.

Once the retainer 30 has been positioned at a desired location relative to the body tissue 40, the portions 32 and 34 of the suture 36 are tensioned with a desired force. The manner in which the portions 32 and 34 of the suture 36 are tensioned with a predetermined force may be the same as is disclosed in U.S. Pat. No. 6,159,234 or in U.S. patent application Ser. No. 09/556,458 filed May 3, 2000 by Peter M. Bonutti and entitled Method And Apparatus For Securing Tissue. Of course, a predetermined tension may be established in the portions 32 and 34 of the suture 36 in a different manner if desired.

While the predetermined tension is maintained in the portions 32 and 34 of the suture, the switch 214 (FIG. 9) is closed and ultrasonic vibratory energy is conducted through the energy transmission member 174 to the retainer 30. The ultrasonic vibratory energy is effective to heat pointed end portions of one or more projections on the retainer 30. This results in a bonding between upper and lower sections of the retainer in the manner previously described in conjunction with the retainers of FIGS. 1-8 and 13-23.

The switch 214 is then released and the flow of ultrasonic vibratory energy to the retainer 30 is interrupted. When this occurs, the retainer cools and an ultrasonic weld is formed between the sections of the retainer. The trigger 198 on the applicator assembly 172 is then actuated to move the force transmitting member 176 axially downward (as viewed in FIG. 24) to release the retainer 30. When the applicator assembly 172 has been disengaged from the retainer 30, it is removed from the cannula 450. The end portions 32 and 34 of the suture 36 may then be cut to a desired length or connected with other body tissue.

Although in the specific embodiment of the invention illustrated in FIG. 24 the suture 36 and retainer 30 are utilized in association with soft body tissue, it is contemplated that the suture 36 and retainer 30 may be used in association with hard body tissue or with both hard and soft body tissue. It is contemplated that the suture 36 may be connected with body tissue in known ways other than the specific way illustrated schematically in FIG. 24. The looping of the suture 36 around the body tissue 40 in FIG. 24 is merely a representation of any one of the many known ways of connecting a suture with body tissue.

Rather than being manually actuated, the applicator assembly 172 may form a portion a robotic mechanism. The robotic mechanism may be operated to tension the suture 36 with a desired tension, slide the retainer 30 along the suture, and transmit energy to the retainer in the manner previously described in conjunction with the applicator assembly 172. The robotic mechanism may be constructed and used in association with imaging devices in the same manner disclosed in U.S. patent application Ser. No. 10/102,413 filed Mar. 20, 2002 by Peter M. Bonutti and entitled Methods of Securing Body Tissue. It is contemplated that the cannula 450 may have any one of many different known constructions, including the constructions disclosed in U.S. Pat. Nos. 6,338,730 and 6,358,266.

Embodiment of FIG. 25

In the embodiment of the invention illustrated in FIG. 12, the applicator assembly 172 is provided with a flange 204 which engages a groove 142 in a retainer 30. In addition, the distal end portion of the applicator assembly 172 of FIGS. 9-12 is exposed so that a retainer gripped between the flange 204 and the end surface 206 on the transmission member 174 is exposed to body fluids. In the embodiment of the invention illustrated in FIG. 25, the distal end portion of the applicator assembly is provided with an end plate rather than a flange and a shield cooperates with the end plate to enclose the retainer. Since the embodiment of the invention illustrated in FIG. 25 is generally similar to the embodiment of the invention illustrated in FIGS. 9-12, similar numerals will be utilized to designate similar components, the suffix letter "h" being associated with the numerals of FIG. 25 to avoid confusion.

An applicator assembly 172h (FIG. 25) includes a tubular force transmitting member 176h. The tubular force transmitting member 176h extends around and is coaxial with an energy transmission member 174h. The energy transmission member 174h has a circular end surface 206h which is engagable with a retainer 30 in a manner similar to that illustrated in FIG. 24.

The metal end plate 464 is connected with the force transmitting member 176h. The metal end plate 464 replaces the flange 204 of the embodiment of the applicator assembly 172 illustrated in FIGS. 9-12 and is effective to apply force against the lower section of a retainer 30 in the manner previously described in conjunction with the retainers of FIGS. 1-8 and 13-23. The end plate 464 eliminates the necessity for the groove 142 in the lower section 46 of the retainer 30 (FIGS. 3-7). In addition, the end plate 464 provides for a relatively even distribution of force against the retainer 30 as it is clamped between the force transmitting member 176 and energy transmission member 174 with a constant predetermined force in the manner illustrated schematically in FIG. 24. The applicator assembly 172h has the same general construction and mode of operation as the applicator assembly 172 of FIGS. 9-12.

In accordance with a feature of the embodiment of the invention illustrated in FIG. 25, a flexible shield 468 is connected with tubular force transmitting member 176. The shield 468 cooperates with the end plate 464 to enclose a retainer 30 gripped between the energy transmission member 174 and the end plate. The proximal end portion 470 of the shield 468 is fixedly connected to the tubular force transmitting member 176. The distal end portion 472 of the shield 468 is free to move relative to the end plate 464 and force transmitting member 176. This provides access to the space between the end plate 464 and the end surface 206 on the energy transmission member 174h to position the retainer 30 between the end plate 464 and the end surface 206h on the energy transmission member 174h.

The shield cooperates with the force transmitting member 176h to enclose the retainer 30. This minimizes exposure of the retainer 30 to body tissue and/or body fluids. However, the flexible material of the shield 468 enables the portions 32 and 34 of the suture 36 to extend from the distal end portion of the applicator assembly 172.

Conclusion

In view of the foregoing description, it is apparent that the present invention relates to a new and improved apparatus and method for use in securing a suture 36. The suture 36 is positioned relative to sections 46 and 48 of an improved retainer 30. The sections 46 and 48 of the retainer 30 are interconnected when the retainer has been positioned relative to a patient's body tissue 40. The sections 46 and 48 of the retainer 30 may be bonded together by the application of energy to the retainer by an improved applicator assembly 172.

The improved retainer 30 may have one or more projections 66 and 68 which engage one or more recesses 58 and 60 to position the sections 46 and 48 of the retainer relative to each other. An interference fit may be provided between one or more projections 66 and 68 and one or more recesses 58 and 60 to hold the sections 46 and 48 of the retainer 30 in a desired spatial relationship. The projections 66 and 68 may have surfaces 88 and 90 which at least partially define one or more passages 52 and 54 and guide movement of one or more portions 32 and 34 of the suture 36 relative 30 to the retainer. In addition, surfaces on the projections may function to position the suture relative to the retainer.

The improved applicator assembly 172 may be used to apply energy to the retainer 30. Energy applied to the retainer 30 may effect bonding of end portions 124 and 126 of the projections 66 and 68 to bottom portions 118 and 120 of recesses 68 and 60 in the retainer 30. The end portions 124 and 126 of the projections 58 and 60 may function as energy directors which concentrate energy. If desired, one or more loops 230 and 232 may be formed in the suture 36 around one or more of the projections 66 and 68.

The applicator assembly may grip the retainer 30 with a predetermined force. While the applicator assembly 172 grips the retainer 30, the applicator assembly may be utilized to slide the retainer along the suture 36 to position the retainer relative to body tissue. While the applicator assembly 172 is gripping the retainer 30, the applicator assembly may apply energy to the retainer to effect bonding of sections 46 and 48 of the retainer together. The applicator assembly 172 may be used to move the retainer 30 into a cannula 450 to engage tissue in a patient's body.

The present invention includes a plurality of different features which may be utilized in combination with each other or separately. The various features of the invention may be used in combination with features of the prior art. For example, the improved retainer 30 may be used with the improved applicator assembly 172 or with a prior art applicator assembly. As another example, the improved applicator assembly 172 may be used with the improved retainer 30 or a prior art retainer. As still another example, the retainer 30 may be moved through a cannula 450 to a desired position relative to body tissue or may be positioned relative to the body tissue without being moved through a cannula.

Having described the invention, the following is claimed:

1. A method for joining a first implant and a second implant, the method comprising:
    positioning the first implant into a body of a patient, the first implant having an upper surface with at least one recess or a plurality of pores and a surface feature configured to contact a portion of a lower surface of the second implant;
    positioning the second implant into the body of the patient, the second implant having a lower surface with a projection and wherein at least the projection of the second implant is configured to contact at least a portion of the upper surface of the first implant;
    applying ultrasonic energy to the second implant to soften at least a portion of the projection or the surface feature at or near a joining region; and
    applying a force to the second implant such that at least a portion of the first or second implant deforms to join the first and second implants at or near the joining region.

2. The method of claim 1 wherein the projection or the surface feature includes an energy director configured to concentrate the ultrasonic energy.

3. The method of claim 1 wherein the at least a portion of the projection or the surface feature is heated into or above its transition temperature range.

4. The method of claim 1 wherein the application of the force is initiated during the application of the ultrasonic energy.

5. The method of claim 1 wherein the application of the force is continued after the application of the ultrasonic energy.

6. The method of claim 1 wherein at least a portion of the projection or the surface feature flows after application of the force is initiated.

7. The method of claim 1 wherein the first implant includes a groove or a second recess.

8. A method for joining a first implant and a second implant, the method comprising:
- providing a first implant having an upper surface with a recess or plurality of pores and a surface feature configured to contact a portion of a lower surface of the second implant;
- providing a second implant having a lower surface with a projection, wherein at least a portion of the second implant is configured to contact at least a portion of the recess or plurality of pores of the upper surface of the first implant;
- applying ultrasonic energy to the second implant to soften at least a portion of the projection or the surface feature; and
- applying a force to the second implant such that at least a portion of the projection or the surface feature deforms to join the first and second implants.

9. The method of claim 8 wherein the projection or the surface feature includes an energy director configured to concentrate the ultrasonic energy.

10. The method of claim 8 wherein the application of the force is initiated during the application of the ultrasonic energy.

11. The method of claim 8 wherein the application of the force is continued after the application of the ultrasonic energy.

12. The method of claim 8 wherein at least a portion of the projection or the surface feature flows after application of the force is initiated.

13. The method of claim 8 wherein the first implant includes a groove or a second recess.

14. The method of claim 8 wherein at least a portion of the projection or the surface feature is heated into or above its transition temperature range.

15. A method for joining a first implant and a second implant, the method comprising:
- passing the first implant into a body of a patient, the first implant having an upper surface with at least one recess or a plurality of pores and a surface feature configured to contact a portion of a lower surface of the second implant;
- passing the second implant into the body of the patient, the second implant having a lower surface with a projection, and wherein the projection of the second implant is configured to contact at least a portion of the recess or plurality of pores of the first implant;
- applying ultrasonic energy to the second implant to thereby soften at least a portion of the projection or the surface feature at or near a joining region; and
- applying a force to the second implant such that the projection or the surface feature deforms to join the first and second implants at or near the joining region.

16. The method of claim 15 wherein the projection or the surface feature includes an energy director configured to concentrate the ultrasonic energy.

17. The method of claim 15 wherein the application of the force is initiated during the application of the ultrasonic energy.

18. The method of claim 15 wherein the application of the force is continued after the application of the ultrasonic energy.

19. The method of claim 15 wherein the material of the projection or the surface feature flows after application of the force is initiated.

20. The method of claim 15 wherein the first implant includes a groove or a second recess.

* * * * *